United States Patent
Deshmukh et al.

(10) Patent No.: US 8,618,073 B2
(45) Date of Patent: Dec. 31, 2013

(54) USE OF MIR-29 FOR CELL PROTECTION

(75) Inventors: Mohanish Deshmukh, Chapel Hill, NC (US); Adam Kole, Chapel Hill, NC (US); Vijay Swahari, Cary, NC (US); Scott Hammond, Pittsboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/811,003

(22) PCT Filed: Jul. 22, 2011

(86) PCT No.: PCT/US2011/044922
§ 371 (c)(1),
(2), (4) Date: Mar. 14, 2013

(87) PCT Pub. No.: WO2012/012676
PCT Pub. Date: Jan. 26, 2012

(65) Prior Publication Data
US 2013/0178514 A1     Jul. 11, 2013

Related U.S. Application Data

(60) Provisional application No. 61/366,709, filed on Jul. 22, 2010.

(51) Int. Cl.
*C12Q 1/68* (2006.01)
*C07H 21/02* (2006.01)
*C07H 21/04* (2006.01)

(52) U.S. Cl.
USPC .......... 514/44 R; 435/6.1; 435/6.14; 536/23.1

(58) Field of Classification Search
USPC ................. 514/44; 536/23.1; 435/6
See application file for complete search history.

(56) References Cited

FOREIGN PATENT DOCUMENTS

EP          2 371 370 A1    10/2011
WO    WO 2008/097277 A2     8/2008

OTHER PUBLICATIONS

International Preliminary Report on Patentability Corresponding to International Application No. PCT/US2011/044922; Date of Mailing: Jan. 31, 2013; 9 Pages.
International Search Report Corresponding to International Application No. PCT/US2011/044922; Date of Mailing: Apr. 27, 2012; 15 Pages.
Kole A.J. et al., "miR-29b is activated during neuronal maturation and targets GH3-only genes to restrict apoptosis", *Genes Dev.* 2011, 25: 125-130.
Shi G. et al., "Upregulated miR-29b promotes neuronal cell death by inhibiting Bcl2L2 after ischemic brain injury", *Exp Brain Res.*, 2012, 216:225-230.
Tabrizi S.J. et al., "T Cell Leukemia/Lymphoma 1 and Galectin-1 Regulate Survival/Cell Death Pathways in Human Naïve and IgM +Memory B Cells through Altering Balances in Bcl-2 Family Proteins", *J Immunol*, 2009;182:1490-1499.

*Primary Examiner* — Terra Cotta Gibbs
(74) *Attorney, Agent, or Firm* — Myers Bigel Sibley & Sajovec, P.A.

(57) ABSTRACT

The present invention relates to the regulation of apoptosis and expression of the BH3-only family of genes by miR-29. The invention further relates to the use of miR-29 to protect cells from apoptosis and to treat disorders associated with apoptosis.

17 Claims, 13 Drawing Sheets

```
                          SEQUENCE LISTING

<160> NUMBER OF SEQ ID NOS: 40

<210> SEQ ID NO 1
<211> LENGTH: 22
<212> TYPE: RNA
<213> ORGANISM: Mus musculus

<400> SEQUENCE: 1
uagcaccauc ugaaaucggu ua                                                22

<210> SEQ ID NO 2
<211> LENGTH: 23
<212> TYPE: RNA
<213> ORGANISM: Mus musculus

<400> SEQUENCE: 2
uagcaccauu ugaaaucagu guu                                               23

<210> SEQ ID NO 3
<211> LENGTH: 22
<212> TYPE: RNA
<213> ORGANISM: Mus musculus

<400> SEQUENCE: 3
uagcaccauu ugaaaucggu ua                                                22
```

```
<210> SEQ ID NO 4
<211> LENGTH: 23
<212> TYPE: RNA
<213> ORGANISM: Mus musculus

<400> SEQUENCE: 4
gcaugucccc ucucuuggug cug                                             23

<210> SEQ ID NO 5
<211> LENGTH: 23
<212> TYPE: RNA
<213> ORGANISM: Mus musculus

<400> SEQUENCE: 5
uguaaggaaa gacauuggug cua                                             23

<210> SEQ ID NO 6
<211> LENGTH: 23
<212> TYPE: RNA
<213> ORGANISM: Mus musculus

<400> SEQUENCE: 6 ccauauagu gugucuggug cuu                                              23

<210> SEQ ID NO 7
<211> LENGTH: 23
<212> TYPE: RNA
<213> ORGANISM: Mus musculus

<400> SEQUENCE: 7
cacuucacag uuucuuggug cua                                             23

<210> SEQ ID NO 8
<211> LENGTH: 23
<212> TYPE: RNA
<213> ORGANISM: Mus musculus

<400> SEQUENCE: 8
cuggccucag gccccuggug cuu                                             23

<210> SEQ ID NO 9
<211> LENGTH: 21
<212> TYPE: RNA
<213> ORGANISM: Mus musculus

<400> SEQUENCE: 9
ccccaacauu gcauggugcu a                                               21

<210> SEQ ID NO 10
<211> LENGTH: 81
<212> TYPE: RNA
<213> ORGANISM: Homo sapiens

<400> SEQUENCE: 10
cuucaggaag cugguuucau augguggguuu agauuuaaau agugauuguc uagcaccauu    60
ugaaaucagu guucuugggg g                                               81

<210> SEQ ID NO 11
<211> LENGTH: 28
<212> TYPE: DNA
<213> ORGANISM: Artificial
<220> FEATURE:
<223> OTHER INFORMATION: PCR primer
```

```
<400> SEQUENCE: 11
tcgagctcct acatgcagcc aggatacg                                          28

<210> SEQ ID NO 12
<211> LENGTH: 28
<212> TYPE: DNA
<213> ORGANISM: Artificial
<220> FEATURE:
<223> OTHER INFORMATION: PCR primer

<400> SEQUENCE: 12
cgctcgagaa gagaaaagcc ctcccttg                                          28

<210> SEQ ID NO 13
<211> LENGTH: 28
<212> TYPE: DNA
<213> ORGANISM: Artificial
<220> FEATURE:
<223> OTHER INFORMATION: PCR primer

<400> SEQUENCE: 13
tcacgcgttt cagctaggcc agaaagga                                          28

<210> SEQ ID NO 14
<211> LENGTH: 28
<212> TYPE: DNA
<213> ORGANISM: Artificial
<220> FEATURE:
<223> OTHER INFORMATION: PCR primer

<400> SEQUENCE: 14
cgctcgaggg gaagccatct ttctttga                                          28

<210> SEQ ID NO 15
<211> LENGTH: 28
<212> TYPE: DNA
<213> ORGANISM: Artificial
<220> FEATURE:
<223> OTHER INFORMATION: PCR primer

<400> SEQUENCE: 15
tcgagctctg tggagtagag gggactgg                                          28

<210> SEQ ID NO 16
<211> LENGTH: 28
<212> TYPE: DNA
<213> ORGANISM: Artificial
<220> FEATURE:
<223> OTHER INFORMATION: PCR primer

<400> SEQUENCE: 16
cgctcgagag actctggccg taccaaga                                          28

<210> SEQ ID NO 17
<211> LENGTH: 28
<212> TYPE: DNA
<213> ORGANISM: Artificial
<220> FEATURE:
<223> OTHER INFORMATION: PCR primer

<400> SEQUENCE: 17
tcgagctcgc ctggctggac taaacctc                                          28
```

<210> SEQ ID NO 18
<211> LENGTH: 28
<212> TYPE: DNA
<213> ORGANISM: Artificial
<220> FEATURE:
<223> OTHER INFORMATION: PCR primer

<400> SEQUENCE: 18
cgctcgagag gagtgttggg aacacagg                                28

<210> SEQ ID NO 19
<211> LENGTH: 32
<212> TYPE: DNA
<213> ORGANISM: Artificial
<220> FEATURE:
<223> OTHER INFORMATION: Mutagenesis primer

<400> SEQUENCE: 19
ccacgcgtca tgtccctctc tcgacagtgt gt                           32

<210> SEQ ID NO 20
<211> LENGTH: 32
<212> TYPE: DNA
<213> ORGANISM: Artificial
<220> FEATURE:
<223> OTHER INFORMATION: Mutagenesis primer

<400> SEQUENCE: 20
acacactgtc gagagaggga catgacgcgt gg                           32

<210> SEQ ID NO 21
<211> LENGTH: 46
<212> TYPE: DNA
<213> ORGANISM: Artificial
<220> FEATURE:
<223> OTHER INFORMATION: Mutagenesis primer

<400> SEQUENCE: 21
gttatgtatg taaggaaaga cattaatgaa gatgagccaa ggctca            46

<210> SEQ ID NO 22
<211> LENGTH: 46
<212> TYPE: DNA
<213> ORGANISM: Artificial
<220> FEATURE:
<223> OTHER INFORMATION: Mutagenesis primer

<400> SEQUENCE: 22
tgagccttgg ctcatcttca ttaatgtctt tccttacata cataac            46

<210> SEQ ID NO 23
<211> LENGTH: 40
<212> TYPE: DNA
<213> ORGANISM: Artificial
<220> FEATURE:
<223> OTHER INFORMATION: Mutagenesis primer

<400> SEQUENCE: 23
ccttacctat atagtgtgtc tcacttcaca gtttcttggt                   40

<210> SEQ ID NO 24
<211> LENGTH: 40
<212> TYPE: DNA
<213> ORGANISM: Artificial
<220> FEATURE:
<223> OTHER INFORMATION: Mutagenesis primer

<400> SEQUENCE: 24
accaagaaac tgtgaagtga gacacactat ataggtaagg                                40

<210> SEQ ID NO 25
<211> LENGTH: 40
<212> TYPE: DNA
<213> ORGANISM: Artificial
<220> FEATURE:
<223> OTHER INFORMATION: Mutagenesis primer

<400> SEQUENCE: 25
tgtctcactt cacagtttct aagtgtatcc ttcttggtac                                40

<210> SEQ ID NO 26
<211> LENGTH: 40
<212> TYPE: DNA
<213> ORGANISM: Artificial
<220> FEATURE:
<223> OTHER INFORMATION: Mutagenesis primer

<400> SEQUENCE: 26
gtaccaagaa ggatacactt agaaactgtg aagtgagaca                                40

<210> SEQ ID NO 27
<211> LENGTH: 34
<212> TYPE: DNA
<213> ORGANISM: Artificial
<220> FEATURE:
<223> OTHER INFORMATION: Mutagenesis primer

<400> SEQUENCE: 27 aatacccccaa cattgcactg aaccccatcc tgtc                                     34

<210> SEQ ID NO 28
<211> LENGTH: 34
<212> TYPE: DNA
<213> ORGANISM: Artificial
<220> FEATURE:
<223> OTHER INFORMATION: Mutagenesis primer

<400> SEQUENCE: 28
gacaggatgg ggttcagtgc aatgttgggg tatt                                      34

<210> SEQ ID NO 29
<211> LENGTH: 59
<212> TYPE: DNA
<213> ORGANISM: Artificial
<220> FEATURE:
<223> OTHER INFORMATION: Cloning primer

<400> SEQUENCE: 29
cgcgtgggtg tccccagtgc gccttcactt tgggcctggc ctcaggcccc tggtgcttc           59

<210> SEQ ID NO 30
<211> LENGTH: 59
<212> TYPE: DNA
<213> ORGANISM: Artificial
<220> FEATURE:
<223> OTHER INFORMATION: Cloning primer

<400> SEQUENCE: 30
tcgagaagca ccaggggcct gaggccaggc ccaaagtgaa ggcgcactgg ggacaccca           59

-continued

```
<210> SEQ ID NO 31
<211> LENGTH: 51
<212> TYPE: DNA
<213> ORGANISM: Artificial
<220> FEATURE:
<223> OTHER INFORMATION: Cloning primer

<400> SEQUENCE: 31
cgcgtgggtg tccccagtgc gccttcactt tgggcctggc ctcaggcccc c        51

<210> SEQ ID NO 32
<211> LENGTH: 51
<212> TYPE: DNA
<213> ORGANISM: Artificial
<220> FEATURE:
<223> OTHER INFORMATION: Cloning primer

<400> SEQUENCE: 32 tcgaggggc ctgaggccag gcccaaagtg aaggcgcact ggggacaccc a          51

<210> SEQ ID NO 33
<211> LENGTH: 23
<212> TYPE: DNA
<213> ORGANISM: Artificial
<220> FEATURE:
<223> OTHER INFORMATION: qRT-PCR primer

<400> SEQUENCE: 33
caagtcaaca caaaccccaa gtc                                        23

<210> SEQ ID NO 34
<211> LENGTH: 20
<212> TYPE: DNA
<213> ORGANISM: Artificial
<220> FEATURE:
<223> OTHER INFORMATION: qRT-PCR primer

<400> SEQUENCE: 34
gtcgtatgga agccattgca                                            20

<210> SEQ ID NO 35
<211> LENGTH: 19
<212> TYPE: DNA
<213> ORGANISM: Artificial
<220> FEATURE:
<223> OTHER INFORMATION: qRT-PCR primer

<400> SEQUENCE: 35
agcggcggag acaagaaga                                             19

<210> SEQ ID NO 36
<211> LENGTH: 26
<212> TYPE: DNA
<213> ORGANISM: Artificial
<220> FEATURE:
<223> OTHER INFORMATION: qRT-PCR primer

<400> SEQUENCE: 36
agtcccatga agagattgta catgac                                     26

<210> SEQ ID NO 37
<211> LENGTH: 20
<212> TYPE: DNA
<213> ORGANISM: Artificial
<220> FEATURE:
<223> OTHER INFORMATION: qRT-PCR primer
```

```
<400> SEQUENCE: 37
tgtgtccgtc gtggatctga                                              20

<210> SEQ ID NO 38
<211> LENGTH: 21
<212> TYPE: DNA
<213> ORGANISM: Artificial
<220> FEATURE:
<223> OTHER INFORMATION: qRT-PCR primer

<400> SEQUENCE: 38
cctgcttcac caccttcttg a                                            21

<210> SEQ ID NO 39
<211> LENGTH: 28
<212> TYPE: DNA
<213> ORGANISM: Artificial
<220> FEATURE:
<223> OTHER INFORMATION: PCR primer

<400> SEQUENCE: 39
gtctcgaggc cacaaaaaca gacgacaa                                     28

<210> SEQ ID NO 40
<211> LENGTH: 26
<212> TYPE: DNA
<213> ORGANISM: Artificial
<220> FEATURE:
<223> OTHER INFORMATION: PCR primer

<400> SEQUENCE: 40
gcgaattcag ggcaggctct ggtagc                                       26
```

USE OF MIR-29 FOR CELL PROTECTION

STATEMENT OF PRIORITY

This application is a 35 U.S.C. §371 national phase application of PCT Application No. PCT/US2011/044922 filed Jul. 22, 2011 which claims the benefit of U.S. Provisional Application Ser. No. 61/366,709, filed Jul. 22, 2010, the entire contents of each of which is incorporated by reference herein.

STATEMENT OF FEDERAL SUPPORT

This invention was made, in part, with government support under grant numbers NS-042197 and F30NS-068006 from the National Institutes of Health. The United States government has certain rights to this invention.

FIELD OF THE INVENTION

The present invention relates to the regulation of apoptosis and expression of the BH3-only family of genes by miR-29. The invention further relates to the use of miR-29 to protect cells from apoptosis and to treat disorders associated with apoptosis.

BACKGROUND OF THE INVENTION

In mammalian cells, apoptosis is triggered when cells encounter cytotoxic stresses, such as nutrient withdrawal or DNA damage. These insults initiate signaling cascades that activate pro-apoptotic BH3-only members of the Bcl-2 family of proteins and cause the release of cytochrome c from the mitochondrial intermembrane space into the cytoplasm (Wang, *Genes Dev.* 15:2922 (2001)). The release of cytochrome c from mitochondria is a key event that triggers the rapid activation of caspases, the key cellular proteases which ultimately execute cell death (Hengartner, *Nature* 407:770 (2000)).

During normal development of the nervous system, a period of massive neuronal apoptosis occurs to precisely match neurons to their respective target cells (Oppenheim, *Annu. Rev. Neurosci.* 14:453 (1991)). However, once appropriate neuronal connections are in place, it is imperative that neurons strictly inhibit their apoptotic program since these cells do not divide, have limited capability for regeneration, and must survive for the lifetime of the organism (Benn et al., *Nat. Rev. Neurosci.* 5:686 (2004)). Although some changes in apoptotic machinery have been identified during neuronal maturation (Putcha et al., *J. Cell Biol.* 149:1011 (2000); Wright et al., *J. Cell Biol.* 179:825 (2007); Walsh et al., *J. Neurosci.* 24:9638 (2004); Tsui-Pierchala et al., *J. Neurosci.* 19:8207 (1999)), it is unclear whether other mechanisms exist in mature neurons to strictly disable their apoptotic program.

MicroRNAs (miRNAs) are small non-coding RNAs that regulate gene expression (Bartel, *Cell* 116:281 (2004)). While mis-expression of some miRNAs has been linked with apoptosis and cancer (Esquela-Kerscher et al., *Nat. Rev. Cancer* 6:259 (2006); Kent et al., *Oncogene* 25:6188 (2006)), very little is known about how miRNAs regulate cell death during normal development.

The present invention addresses previous shortcomings in the art by identifying a regulatory role for miR-29 in the expression of the BH3-only family of genes and control of apoptosis in cells and providing methods for inhibiting apoptosis in cells.

SUMMARY OF THE INVENTION

The present invention is based, in part, on the identification of the regulatory role played by miR-29 (e.g., miR-29b) in the expression of the BH3-only family of genes. It has surprisingly been discovered that miR-29 can target multiple genes in the functionally redundant BH3-only family to regulate cell sensitivity to apoptosis. The discovery that increased levels of miR-29 in neurons enhances the resistance of the neurons to apoptotic signals provides methods for protecting neurons and other cells (e.g., post-mitotic cells) from apoptosis and treating and/or preventing disorders associated with apoptosis (e.g., neurodegenerative processes associated with neuronal apoptosis and disorders associated with apoptosis of skeletal or cardiac muscle cells).

Accordingly, as one aspect, the invention provides a method of inhibiting expression of one or more BH3-only genes in a cell (e.g., a post-mitotic cell), comprising increasing the amount of miR-29 in the cell.

Another aspect of the invention relates to a method of treating and/or preventing a disorder associated with apoptosis in a subject, comprising increasing the amount of miR-29 in a cell of the subject.

A further aspect of the invention relates to a method of treating and/or preventing cell damage (e.g., neuronal damage) due to an ischemic event or trauma in a subject, comprising increasing the amount of miR-29 in a cell (e.g., neuron) of the subject.

Another aspect of the invention relates to a method of determining the sensitivity of a cell to apoptosis, comprising measuring the level of miR-29 in the cell.

One aspect of the invention relates to methods of identifying a compound that modulates the level of miR-29 in a cell, comprising determining the level of miR-29 in the presence and absence of a test compound, and selecting a compound that increases or decreases the level of miR-29 relative to the level in the absence of the compound, as a compound that modulates the level of miR-29 in a cell.

Another aspect of the invention relates to methods of identifying a compound useful for protecting cells against apoptosis, comprising determining the level of miR-29 in the presence and absence of a test compound, and selecting a compound that increases the level of miR-29 relative to the level in the absence of the compound, as a compound useful for protecting cells against apoptosis.

An additional aspect of the invention relates to a pharmaceutical composition comprising a miR-29 polynucleotide.

A further aspect of the invention relates to a transgenic non-human animal that recombinantly expresses a miR-29 polynucleotide.

These and other aspects of the invention are set forth in more detail in the description of the invention below.

DETAILED DESCRIPTION OF THE INVENTION

Figure 1:
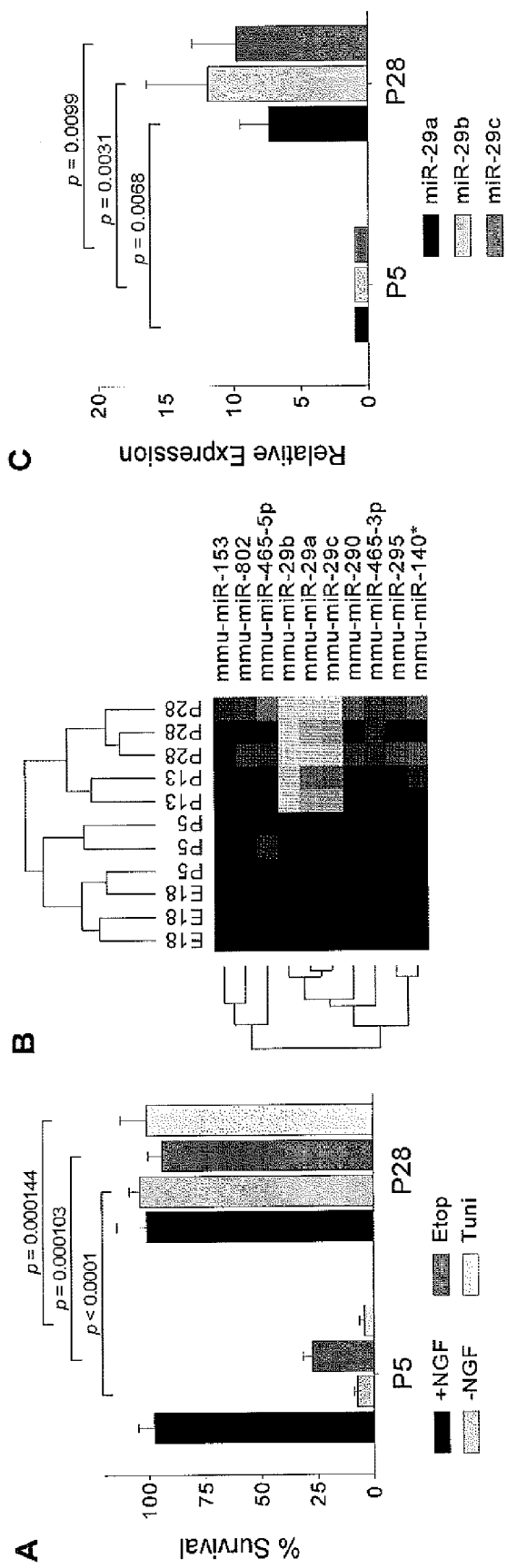
FIGS. 1A-1C show neuronal maturation is associated with a marked increase in miR-29 and restriction of apoptosis. A) P0 sympathetic neurons were cultured for 5 days (P5) or 28 days (P28) in vitro and either maintained in NGF-containing media (+NGF), deprived of NGF (−NGF), treated with 20 µM etoposide to induce DNA damage (Etop), or treated with 2.5 µM tunicamycin to induce ER stress (Tuni) for 72 hrs. Cell survival was quantified by cell morphology and was expressed as a percentage of viable cells prior to cell treatment. B) miRNA microarray expression data for sympathetic ganglia isolated from E18, P5, P13 and P28 mice. Data were $\log_2$ normalized and hierarchically clustered by sample and plotted as a heat map. A light color denotes high expression and a dark color denotes low expression. C) qRT-PCR for miR-29a, miR-29b, and miR-29c using RNA collected from P0 sympathetic neurons maintained in culture for 5 days (P5) of 28 days (P28). Expression of each miRNA is plotted relative to levels in P5 neurons. Data in (A) and (C) are mean±s.d. of three independent experiments.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even±0.1% of the specified amount.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP §2111.01 Thus, the term "consisting essentially of" as used herein should not be interpreted as equivalent to "comprising."

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

"Prevent" or "preventing" or "prevention" refer to prevention or delay of the onset of the disorder and/or a decrease in the severity of the disorder in a subject relative to the severity that would develop in the absence of the methods of the invention. The prevention can be complete, e.g., the total absence of ischemia in a subject. The prevention can also be partial, such that the occurrence of ischemia in a subject is less than that which would have occurred without the present invention.

The term "increasing the amount of miR-29," as used herein, refers to an increase in the level of functional miR-29 RNA within a cell. The term encompasses increasing the level of miR-29 from the normal level in the cell to a higher level as well as increasing the level from a level that is below normal to a level that is normal or higher than normal.

The term "miR-29," as used herein, refers to a microRNA in the human miR-29 family, including miR-29a, miR-29b, and miR-29c. The term includes miR-29, pri-miR-29, pre-miR-29, and mature miR-29. The term also includes sequence variants of members of the miR-29 family (e.g., 1 2, 3, 4, 5, or more variant nucleotides) as long as the variant substantially retains the biological activity of the wild-type miR-29. The term also includes variants that have been modified to resist degradation within a subject and/or within a cell. The term further includes fragments of a miR-29 microRNA that substantially retain the biological activity of the wild-type miR-29. The term "substantially retains the biological activity" is defined as a level of at least one biological activity (e.g., inhibition of expression of a BH3-only gene) of at least 50% of the activity of the wild-type sequence.

The term "precursor of miR-29," as used herein, refers to a form of miR-29 that is processed into mature miR-29. Precursors of miR-29 include pri-miR-29, pre-miR-29, and any other polynucleotide sequence that can be processed in a cell to produce mature miR-29.

The term "miR-29 polynucleotide," as used herein, refers to a polynucleotide that is miR-29 or encodes miR-29. The polynucleotide can be a RNA, a DNA, or a hybrid of RNA and DNA.

The term "BH3-only family of genes" or "BH3-only genes," as used herein, refers to any member of the art-recognized family of genes encoding a BCL2-related protein comprising a BCL2 homology 3 (BH3) domain but not any other BH domains and is involved in apoptosis. In one embodiment, the term refers to BH3-only genes that are pro-apoptotic. In another embodiment, the term refers to the family members that comprise a miR-29 target sequence. In another embodiment, the members are bim, hrk, bmf, puma, N-bak, and any combination thereof.

The term "inhibiting expression of one or more BH3-only genes," as used herein, refers to a decrease in the level of RNA and/or protein encoded by one or more BH3-only genes.

The term "disorder related to apoptosis," as used herein, refers to any disease, disorder, or condition that is caused by and/or includes symptoms that are caused by apoptosis of cells.

The term "resistance of a cell to an apoptotic signal," as used herein, refers to the ability of a cell to survive a signal that would normally send the cell into the apoptotic process and result in cell death.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

An "isolated cell" refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and/or adenovirus vectors. Non-viral vectors include, but are not limited to, plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Felgner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, $\beta$-glucuronidase, $\beta$-galactosidase, luciferase, etc.), hemagglutinin, c-myc, FLAG epitope, etc.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

Methods of Protection Against Apoptosis

As one aspect, the invention provides a method of inhibiting expression of one or more BH3-only genes in a cell, comprising increasing the amount of miR-29 in the cell. In certain embodiments, 1, 2, 3, 4, 5 or more BH3-only genes are inhibited by the increase in miR-29. The BH3-only gene can be any BH3-only gene now known or identified in the future, particularly BH3-only genes that are expressed in neurons or other post-mitotic cells. In another embodiment, the BH3-only genes are those that comprise a miR-29 target sequence. In certain embodiments, the BH3-only gene is selected from the group consisting of him, hrk, bmf, puma, N-bak, and any combination thereof. The method can be carried out for research purposes or therapeutic purposes.

In one embodiment, the cell is a post-mitotic cell, i.e., a mature cell that is no longer capable of undergoing mitosis. Post-mitotic cells include, without limitation, neurons, skeletal and cardiac muscle cells (e.g., myotubes, myonuclei, cardiomyocytes), islet $\beta$-cells, photoreceptors, corneal endothelium, and sensory hair cells. In certain embodiments, the neuron can be a neuron of the central nervous system, e.g., a cerebellar neuron, a cortical neuron, or a motor neuron. In other embodiments, the neuron can be a neuron of the peripheral nervous system, e.g., a sympathetic neuron or a dorsal root ganglia neuron. The cell can be a cell in vitro, ex vivo, or in vivo. The cell can be from established cell lines or primary cells from a subject, e.g., a research animal or a patient.

Another aspect of the invention relates to a method of increasing the resistance of a cell (e.g., a neuron) to an apoptotic signal, comprising increasing the amount of miR-29 in the cell. The apoptotic signal can be any signal known to cause apoptosis in cells. For example, the apoptotic signal can be one specific to a cell type (e.g., withdrawal of a neuronal growth factor such as NGF) or one that is more general (e.g., DNA damage, oxidative stress, ER stress).

A further aspect of the invention relates to a method of treating and/or preventing a disorder associated with apoptosis in a subject, comprising increasing the amount of miR-29 in a cell of the subject. In certain embodiments, the method encompasses treatment of a disorder to alleviate one or more symptoms and/or to slow down or stop the progression of the disorder. In other embodiments, the method encompasses a subject that has not yet developed a disorder (e.g., a subject at risk for developing a disorder) or is in an early stage of the disorder and the method delays onset of the disorder or delays progression of the disorder to a more advanced stage.

In one embodiment, the disorder is a neurological disorder (e.g., one that is related to apoptosis) and the method comprises increasing the amount of miR-29 in a neuron of the subject. The neurological disorder can be a neurodegenerative disorder, which includes, without limitation, trigeminal neuralgia, glossopharyngeal neuralgia, Bell's palsy, cerebral palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone, ticks, porphyria, Guillain-Barre syndrome, dementia, Alzheimer's disease, Parkinson's disease, and Huntington's chorea. In another embodiment, the neurological disorder can be, for example, epilepsy, spinal cord injury, stroke, or traumatic brain injury.

In another embodiment, the disorder is a muscular disorder (e.g., skeletal or cardiac) and the method comprises increasing the amount of miR-29 in a muscle cell of the subject. The disorder can be any disorder involving apoptosis of muscle cells and includes, without limitation, chronic heart failure, skeletal muscle denervation, spinal cord injury, muscular dystrophy, myotonia congenita, myotonic dystrophy, spinal muscular atrophy, muscle atrophy due to immobilization, sarcopenia, myopathy, sepsis, starvation, obesity, cancer, and cachexia. In a further embodiment, the disorder is one related to pancreatic islet cells and insulin, e.g., diabetes (type 1 or type 2).

An additional aspect of the invention relates to a method of treating and/or preventing cell (e.g., neuronal) damage due to an ischemic event or trauma in a subject, comprising increasing the amount of miR-29 in a cell of the subject. The method encompasses treatment of an ischemic event or trauma that has already occurred to alleviate one or more symptoms. In other embodiments, the method encompasses a subject that has not yet had an ischemic event or trauma but is at risk for an event (e.g., a subject about to undergo neurosurgery or that has had a blood clot and/or been administered blood thinners). In certain embodiments, the ischemic event can be a stroke. In certain embodiments, the trauma can be a traumatic brain injury or a spinal cord injury.

The miR-29 microRNA can be any member of the miR-29 family, e.g., miR-29a, miR-29b, or miR-29c. In one embodiment, the miR-29 is a human miR-29, e.g., an RNA molecule comprising, consisting essentially of or consisting of miR-29a, miR-29b, or miR-29c (SEQ ID NOS:1-3) or a fragment or variant thereof that substantially maintains the biological activity of the wild-type sequence. Known sequences for miR-29 are listed in the miRBase database, and human miR-29 sequences are found at accession numbers MI0000087, MI000105, MI0000107, and MI0000735, incorporated by reference herein in their entirety. For example, the sequence of human pre-miR-29b is listed below with the mature miR-29b sequence underlined.

(SEQ ID NO: 10)
CUUCAGGAAGCUGGUUUCAUAUGGUGGUUUAGAUUUAAAUAGUGAUUGUC

UAGCACCAUUUGAAAUCAGUGUUCUUGGGGG

A microRNA can be constructed using chemical synthesis and enzymatic ligation reactions by procedures known in the art. For example, a microRNA can be chemically synthesized using naturally occurring nucleotides or various modified nucleotides designed to increase the biological stability of the molecules or to increase the physical stability of the duplex formed between the microRNA and target nucleotide sequences, e.g., phosphorothioate derivatives and acridine substituted nucleotides can be used. Examples of modified nucleotides which can be used to generate the microRNA include, but are not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the microRNA can be produced using an expression vector into which a nucleic acid encoding the microRNA has been cloned.

The microRNA can further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the microRNA is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., *Nucleic Acids Res.* 17:9193 (1989); Agrawal et al., *Proc. Natl. Acad. Sci. USA* 87:1401 (1990); Baker et al., *Nucleic Acids Res.* 18:3537 (1990); Sproat et al., *Nucleic Acids Res.* 17:3373 (1989); Walder and Walder, *Proc. Natl. Acad. Sci. USA* 85:5011 (1988); incorporated by reference herein in their entireties for their teaching of methods of making polynucleotide molecules, including those containing modified nucleotide bases).

The miR-29 microRNA of the invention can be delivered directly into a cell by any method known in the art, e.g., by transfection or micro injection. In other embodiments, the microRNA can be delivered to a subject in the form of polynucleotides encoding the RNA to produce expression of the microRNA or a microRNA precursor within the cells of the subject. Those skilled in the art will appreciate that the isolated polynucleotides encoding the RNAs of the invention will typically be associated with appropriate expression control sequences, e.g., transcription/translation control signals and polyadenylation signals.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the polypeptide coding sequence can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et al., *Gene Ther.*, 4:432 (1997)); and the rapamycin-inducible system (Magari et al., *J. Clin. Invest.* 100: 2865 (1997)).

Other tissue-specific promoters or regulatory promoters include, but are not limited to, promoters that typically confer tissue-specificity in neurons. These include, but are not limited to, promoters for synapsin 1, tubulin α1, platelet-derived growth factor B-chain, tyrosine hydroxylase, neuron-specific enolase, and neurofilaments. Skeletal muscle cell promoters include, but are not limited to, promoters for β-actin, Pitx3, creatine kinase, and myosin light chain. Cardiac muscle cell promoters include, but are not limited to, promoters for cardiac actin, cardiac troponin T, troponin C, myosin light chain-2, and α-myosin heavy chain. Islet (beta) cell promoters include, but are not limited to, glucokinase, gastrin, insulin, and islet amyloid polypeptide.

Moreover, specific initiation signals are generally required for efficient translation of inserted polypeptide coding sequences. These translational control sequences, which can include the ATG initiation codon and adjacent sequences, can be of a variety of origins, both natural and synthetic.

The isolated polynucleotide encoding miR-29 can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a microRNA operatively associated with the promoter, and, optionally, a termination sequence including a stop signal for RNA polymerase and a polyadenylation signal for polyadenylase.

Non-limiting examples of promoters of this invention include, but are not limited to, CYC1, HIS3, GAL1, GAL4, GAL10, ADH1, PGK, PHO5, GAPDH, ADC1, TRP1, URA3, LEU2, ENO, TPI, and alkaline phosphatase promoters (useful for expression in *Saccharomyces*); AOX1 promoter (useful for expression in *Pichia*); β-lactamase, lac, ara, tet, trp, IP$_L$, IP$_R$, T7, tac, and trc promoters (useful for expression in *Escherichia coli*); light regulated-, seed specific-, pollen specific-, ovary specific-, pathogenesis or disease related-promoters, cauliflower mosaic virus 35S, CMV 35S minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro baciliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), and pathogenesis and/or disease-related promoters. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

It will be apparent to those skilled in the art that any suitable vector can be used to deliver the polynucleotide to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Suitable vectors include, but are not limited to, plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like.

Any viral vector that is known in the art can be used in the present invention. Protocols for producing recombinant viral vectors and for using viral vectors for nucleic acid delivery can be found in Ausubel et al., Current Protocols in Molecular Biology (Green Publishing Associates, Inc. and John Wiley & Sons, Inc., New York) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, polylysine conjugates, and artificial viral envelopes.

In particular embodiments, plasmid vectors are used in the practice of the present invention. For example, naked plasmids can be introduced into muscle cells by injection into the tissue. Expression can extend over many months, although the number of positive cells is typically low (Wolff et al., *Science* 247:247 (1989)). Cationic lipids have been demonstrated to aid in introduction of nucleic acids into some cells in culture (Felgner and Ringold, *Nature* 337:387 (1989)). Injection of cationic lipid plasmid DNA complexes into the circulation of mice has been shown to result in expression of the DNA in lung (Brigham et al., *Am. J. Med. Sci.* 298:278 (1989)). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., *No Shinkei Geka* 20:547 (1992); PCT publication WO 91/06309; Japanese patent application 1047381; and European patent publication EP-A-43075).

Liposomes that consist of amphiphilic cationic molecules are useful as non-viral vectors for nucleic acid delivery in vitro and in vivo (reviewed in Crystal, *Science* 270:404 (1995); Blaese et al., *Cancer Gene Ther.* 2:291 (1995); Behr et al., *Bioconjugate Chem.* 5:382 (1994); Remy et al., *Bioconjugate Chem.* 5:647 (1994); and Gao et al., *Gene Therapy* 2:710 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid: nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Felgner et al., *Proc. Natl. Acad. Sci. USA* 84:7413 (1987); Loeffler et al., *Meth. Enzymol.* 217:599 (1993); Felgner et al., *J. Biol. Chem.* 269:2550 (1994)).

Several groups have reported the use of amphiphilic cationic lipid:nucleic acid complexes for in vivo transfection both in animals and in humans (reviewed in Gao et al., *Gene Therapy* 2:710 (1995); Zhu et al., *Science* 261:209 (1993); and Thierry et al., *Proc. Natl. Acad. Sci. USA* 92:9742 (1995)). U.S. Pat. No. 6,410,049 describes a method of preparing cationic lipid:nucleic acid complexes that have a prolonged shelf life.

Nuclear localization signals can also be used to enhance the targeting of the microRNA or expression vector into the proximity of the nucleus and/or its entry into the nucleus. Such nuclear localization signals can be a protein or a peptide such as the SV40 large Tag NLS or the nucleoplasmin NLS. These nuclear localization signals interact with a variety of nuclear transport factors such as the NLS receptor (karyopherin alpha) which then interacts with karyopherin beta.

Expression vectors can be designed for expression of microRNAs in prokaryotic or eukaryotic cells. For example, microRNAs can be expressed in bacterial cells such as *E. coli*, insect cells (e.g., the baculovirus expression system), yeast cells, plant cells or mammalian cells. Some suitable host cells are discussed further in Goeddel, *Gene Expression Technology*: Methods in Enzymology 185, Academic Press, San Diego, Calif. (1990). Examples of bacterial vectors include, but are not limited to, pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSecl (Baldari et al., *EMBO J.* 6:229 (1987)), pMFa (Kurjan and Herskowitz, *Cell* 30:933 (1982)), pJRY 88 (Schultz et al., *Gene* 54:113 (1987)), and pYES2 (Invitrogen Corporation, San Diego, Calif.). Non-limiting examples of baculovirus vectors available for expression of nucleic acids to produce proteins in cultured insect cells (e.g., Sf 9 cells) include the pAc series (Smith et al., *Mol. Cell. Biol.* 3:2156 (1983)) and the pVL series (Lucklow and Summers *Virology* 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, *Nature* 329:840 (1987)) and pMT2PC (Kaufman et al., *EMBO J.* 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-limiting examples of non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including, but are not limited to, calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

In certain embodiments of the invention, the level of miR-29 in a cell can be increased by delivering to the cell a compound that raises the level of miR-29. Suitable compounds can be identified by screening assays as described below.

In one embodiment, the miR-29 polynucleotides of the invention are administered directly to the subject. Generally, the compounds of the invention will be suspended in a pharmaceutically-acceptable carrier (e.g., physiological saline) and administered orally, topically, or by intravenous infusion, or injected subcutaneously, intramuscularly, intracranially, intrathecally, intraperitoneally, intrarectally, intravaginally, intranasally, intragastrically, intratracheally, or intrapulmonarily. They are preferably delivered directly to the site of the disease or disorder, such as the brain or spinal cord. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 µg/kg. Wide variations in the needed dosage are to be expected in view of the differing efficiencies of various routes of administration. For example, oral administration would be expected to require higher dosages than administration by i.v. injection (e.g., 2-, 3-, 4-, 6-, 8-, 10-; 20-, 50-, 100-, 150-, or more fold). Variations in these dosage levels can be adjusted using standard empirical routines for optimization as is well understood in the art. Administrations can be single or multiple. Encapsulation of the inhibitor in a suitable delivery vehicle (e.g., polymeric microparticles or implantable devices) may increase the efficiency of delivery, particularly for oral delivery.

According to certain embodiments, the miR-29 polynucleotides can be targeted to specific cells or tissues in vivo. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al., *J. Biol. Chem.* 262:13979 (1987); Ho et al., *J. Biol. Chem.* 262:13973 (1987); and U.S. Pat. No. 4,957,735 to Huang et al., each of which is incorporated herein by reference in its entirety). Enveloped viral vectors can be modified to deliver a nucleic acid molecule to a target cell by modifying or substituting an envelope protein such that the virus infects a specific cell type. In adenoviral vectors, the gene encoding the attachment fibers can be modified to encode a protein domain that binds to a cell-specific receptor. Herpesvirus vectors naturally target the cells of the central and peripheral nervous system. Alternatively, the route of administration can be used to target a specific cell or tissue. For example, intracoronary administration of an adenoviral vector has been shown to be effective for the delivery of a gene to cardiac myocytes (Maurice et al., *J. Clin. Invest.* 104:21 (1999)). Intravenous delivery of cholesterol-containing cationic liposomes has been shown to preferentially target pulmonary tissues (Liu et al., *Nature Biotechnol.* 15:167 (1997)), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

The miR-29 polynucleotides of the present invention can optionally be delivered in conjunction with other therapeutic agents. The additional therapeutic agents can be delivered concurrently with the microRNAs of the invention. As used herein, the word "concurrently" means sufficiently close in time to produce a combined effect (that is, concurrently can be simultaneously, or it can be two or more events occurring within a short time period before or after each other). In one embodiment, the microRNAs of the invention are administered in conjunction with agents useful for treating neurodegenerative disorders and other disorders associated with neuronal apoptosis, such as caprylidene, donepezil, galantamine, tacrine, vitamin E, ergoloid mesylates, rivastigmine, nadolol, zonisamide, amantadine, apomorphine, belladonna, benztropine, biperiden, bromocriptine, carbidopa, entacapone, levodopa, pergolide mesylate, pramipexole, procyclidine, rasagiline, ropinirole, rotiotine, scopolamine, tolcapone, trihexylphenidyl, seleginline, baclofen, pregabalin, tetrabenazine, methylprednisolone, desvenlafaxine, nortriptyline, and haloperidol or a combination thereof.

Diagnostic Methods

The identification of a role for miR-29 in the protection of cells from apoptotic signals can be used advantageously to identify cells that are more susceptible or less susceptible to apoptosis in response to apoptotic signals. Thus, one aspect of the invention relates to a method of determining the sensitivity of a cell to apoptosis, comprising measuring the level of miR-29 in the cell. In one embodiment, the determining step can be carried out on a cell in vitro. The cell can be from a sample (e.g., a tissue sample) from a subject. In one embodiment, the sample is from a diseased tissue such as neuronal tissue, e.g., from a subject suffering from a neurodegenerative disease. In another embodiment, the sample is not from a diseased tissue, e.g., from a subject that is at risk for a disease or is being screened for a disease.

The method can further comprise a step of comparing the measured level to a reference level. The reference level can be from a control sample. The control sample may be from a normal (i.e., non-diseased) portion of the same tissue or cell type in the subject, from a different tissue or cell type in the subject, from a matched individual, or may be a standard derived from the average of measurements taken from a population of subjects. In another embodiment, the control sample may be from the disease tissue of the subject, e.g., at the time of diagnosis, prior to treatment, or after a stage of treatment.

In a further embodiment, the control sample is a cell that has not reached the post-mitotic state.

In one aspect, the reference level of miR-29 is the level in cells (e.g., post-mitotic cells) of normal tissue. If the miR-29 level in the cell is lower than the reference level, the cell has an increased sensitivity to apoptosis. If the miR-29 level in the cell is higher than the reference level, the cell has a decreased sensitivity to apoptosis.

In certain embodiments, a baseline level of miR-29 may be determined upon the initial diagnosis of a disorder or prior to a first treatment (e.g., delivery of miR-29 to the subject). After a baseline is established, the level may be determined repeatedly, e.g., on a regular schedule (e.g., once every 2, 3, 4, 5, or 6 days, 1, 2, 3, or 4 weeks, or more) or as desired (e.g., after each therapeutic treatment). The information obtained from the monitoring may be used to modify the treatment the subject is receiving.

The tissue sample may be obtained by any method known in the art, such as surgery, biopsy, lavage, aspiration, etc. The sample may be a bodily fluid, e.g., blood, serum, plasma, saliva, urine, cerebrospinal fluid, perspiration, etc. In one embodiment, the tissue sample is neural tissue, e.g., from the brain. In other embodiments, the tissue sample is muscle tissue.

The level of miR-29 in a cell can be determined by any method known in the art for detecting and quantitating a polynucleotide, including as described herein. Examples of methods include, without limitation, Northern blots, dot blots, PCR, RT-PCR, quantitative PCR, sequence analysis, gene microarray analysis, in situ hybridization, and detection of a reporter gene. Assays can be carried out automatically or partially automatically in a machine or apparatus designed to perform such assays, e.g., using computer-assisted methods. The results of the assays can be stored in a computer database and analyzed to produce diagnostic results. In some embodiments, the diagnostic data can be analyzed, e.g., by comparing intra-patient results over time or before and after treatment or comparing inter-patient results to determine baseline and/or abnormal values in a population.

One aspect of the invention relates to kits useful for carrying out the methods of the invention. One embodiment relates to kits for determining the level of miR-29 in a cell. The kits may contain reagents for measuring miR-29 levels. The reagents may be nucleic acids (e.g., an oligonucleotide that specifically hybridizes to miR-29 and can be used as a hybridization probe or an amplification primer) or other agents that specifically recognize miR-29.

The reagents can be conjugated to a detectable tag or detectable label. Such a tag can be any suitable tag which allows for detection of the reagents and includes, but is not limited to, any composition or label detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in amplification assays), and colorimetric labels such as colloidal gold or colored glass or plastic (e.g., polystyrene, polypropylene, latex, etc.) beads.

In addition, the reagents can be immobilized on a substrate. Such a substrate can include any suitable substrate for immobilization of a detection reagent such as would be used in any of the previously described methods of detection. Briefly, a substrate suitable for immobilization of a detection reagent includes any solid support, such as any solid organic, biopolymer or inorganic support that can form a bond with the detection reagent without significantly effecting the activity and/or ability of the detection reagent to detect the desired target molecule. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and $NiO$) and sand.

The kits may further comprise other components useful for polynucleotides, e.g., buffers, cells, culture medium, enzymes, labeling reagents, containers, etc.

In one embodiment, the kit comprises an array of reagents for determining microRNA levels. The array can comprise a substrate having a plurality of addresses. At least one address of the plurality includes a capture probe that binds specifically to a one or more miRNAs. The array may comprise capture probes corresponding to miR-29a, miR-29b, and miR-29c as well as other microRNAs (e.g., microRNAs involved in regulation of apoptosis). The substrate can be a two-dimensional substrate such as a glass slide, a wafer (e.g., silica or plastic), a mass spectroscopy plate, or a three-dimensional substrate such as a gel pad. Addresses in addition to addresses of the plurality can be disposed on the array.

In one embodiment, at least one address of the plurality includes a nucleic acid capture probe that hybridizes specifically to a microRNA. Each address of the subset can include a capture probe that hybridizes to a different region of a polynucleotide. An array can be generated by any of a variety of methods. Appropriate methods include, e.g., photolithographic methods (e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

Pharmaceutical Compositions

As a further aspect, the invention provides pharmaceutical formulations and methods of administering the same to achieve any of the therapeutic effects (e.g., inhibition of apoptosis) discussed above. The pharmaceutical formulation may comprise any of the reagents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The microRNAs or vectors encoding microRNAs of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the microRNA (including the physiologically acceptable salts thereof) is typically admixed with, inter alia, an acceptable carrier. The carrier can be a solid or a liquid, or both, and is preferably formulated with the microRNA as a unit-dose formulation, for example, a tablet, which can contain from 0.01 or 0.5% to 95% or 99% by weight of the microRNA. One or more microRNAs can be incorporated in the formulations of the invention, which can be prepared by any of the well-known techniques of pharmacy.

A further aspect of the invention is a method of treating subjects in vivo, comprising administering to a subject a pharmaceutical composition comprising a microRNA of the invention in a pharmaceutically acceptable carrier, wherein the pharmaceutical composition is administered in a therapeutically effective amount. Administration of the microRNAs of the present invention to a human subject or an animal in need thereof can be by any means known in the art for administering compounds.

Non-limiting examples of formulations of the invention include those suitable for oral, rectal, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intracranial, intrathecal, and inhalation administration, administration to the liver by intraportal delivery, as well as direct organ injection (e.g., into the liver, into a limb, into the brain or spinal cord for delivery to the central nervous system, into the pancreas, or into a tumor or the tissue surrounding a tumor). The most suitable route in any given case will depend on the nature and severity of the condition being treated and on the nature of the particular compound which is being used. In some embodiments, it may be desirable to deliver the formulation locally to avoid any side effects associated with systemic administration. For example, local administration can be accomplished by direct injection at the desired treatment site, by introduction intravenously at a site near a desired treatment site (e.g., into a vessel that feeds a treatment site). In some embodiments, the formulation can be delivered locally to ischemic tissue. In certain embodiments, the formulation can be a slow release formulation, e.g., in the form of a slow release depot.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones,

*Drug Delivery to the Respiratory Tract*, Ellis Horwood (1987); Gonda (1990) Critical Reviews in *Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of a neurodegenerative disorder, ischemia, or trauma. In certain embodiments, the subject has or is at risk for a neurodegenerative disorder, ischemia, or trauma.

Screening Methods and Animal Models

The identification of the role of miR-29 in protecting cells from apoptosis can be used advantageously to screen for agents that modulate the level of miR-29 in a cell and regulate apoptosis as well as models for studying the process of apoptosis in vitro or in animals.

One aspect of the invention relates to methods of identifying a compound that modulates the level of miR-29 in a cell, comprising determining the level of miR-29 in the presence and absence of a test compound, and selecting a compound that increases or decreases the level of miR-29 relative to the level in the absence of the compound, as a compound that modulates the level of miR-29 in a cell.

Another aspect of the invention relates to methods of identifying a compound useful for protecting cells against apoptosis, comprising determining the level of miR-29 in the presence and absence of a test compound, and selecting a compound that increases the level of miR-29 relative to the level in the absence of the compound, as a compound useful for protecting cells against apoptosis.

The cell may be contacted with the compound in vitro (e.g., in a culture dish) or in an animal (e.g., a transgenic animal or an animal model). In one embodiment, the detected increase or decrease in level of miR-29 is statistically significant, e.g., at least $p<0.05$, e.g., $p<0.01$, 0.005, or 0.001. In another embodiment, the detected increase or decrease is at least about 10%, 20%, 30%, 40%, 50%, 60%, 70%, 80%, 90%, 100% or more.

The compound can directly interact with miR-29 and thereby modulate its level. Alternatively, the compound can interact with any other polypeptide, nucleic acid or other molecule as long as the interaction results in a modulation of the level of miR-29. To illustrate, the compound can modulate transcription of the gene (or transgene) or modulate the accumulation of microRNA (e.g., by affecting the rate of transcription and/or turnover of the microRNA.

Any compound of interest can be screened according to the present invention. Suitable test compounds include organic and inorganic molecules. Suitable organic molecules can include but are not limited to small molecules (compounds less than about 1000 Daltons), polypeptides (including enzymes, antibodies, and Fab' fragments), carbohydrates, lipids, coenzymes, and nucleic acid molecules (including DNA, RNA, and chimerics and analogs thereof) and nucleotides and nucleotide analogs.

Further, the methods of the invention can be practiced to screen a compound library, e.g., a small molecule library, a combinatorial chemical compound library, a polypeptide library, a cDNA library, a library of antisense nucleic acids, and the like, or an arrayed collection of compounds such as polypeptide and nucleic acid arrays.

Any suitable cell can be used in the assay, including bacteria, yeast, insect cells (e.g., with a baculovirus expression system), avian cells, mammalian cells, or plant cells. In exemplary embodiments, the assay is carried out in a cell line that naturally expresses miR-29, e.g., post-mitotic cells. Further, in other embodiments, it is desirable to use nontransformed cells (e.g., primary cells) as transformation may alter the function of miR-29. In one embodiment, the cell may be a primary cell, e.g., a neuron or muscle cell. In another embodiment, the cell is from a cell line, e.g., a neural cell line or a muscle cell line. Neural cells and cell lines include, without limitation, PC12, HCN-1, SK-N-SH, SK-N-MC, SH-SY5Y, N1E-115, NG108-15, U-87 MG, U-373 MG, GL-15, H4, MO3.13, CHME-5, Daoy, TE-671, LAN-1, A673, and GT1-7. Muscle cells and cell lines include, without limitation, hSkMC, L6, C2C12, HL-1, C2, XM13A1, RCMH, MM14, C17-S1-D-T984, H9C2.

The miR-29 can be endogenously produced in the cell. Alternatively or additionally, the cell can be modified to comprise an isolated polynucleotide encoding, and optionally overexpressing, miR-29. According to this embodiment, the cell can be transiently or stably transformed with a polynucleotide encoding miR-29, but is preferably stably transformed, for example, by stable integration into the genome of the organism or by expression from a stably maintained episome (e.g., Epstein Barr Virus derived episomes). In another embodiment, a polynucleotide encoding a reporter molecule can be linked to a regulatory element of miR-29 and used to identify compounds that modulate expression of the microRNA. In a further embodiment, a reporter molecule can be constructed by cloning one or miR-29 binding sites downstream of a reporter gene (e.g., luciferase). The construct can be transfected into a cell line, which is then contacted with compounds to identify compounds that reduce the luciferase signal (increase miR-29 levels) or increase the luciferase signal (decrease miR-29 levels). Another example of a luciferase-based reporter construct is described in Young et al., *J. Am. Chem. Soc.* 132:7976 (2010)), incorporated herein by reference in its entirety.

Screening assays also can be carried out in vivo in animals. Thus, as still a further aspect, the invention provides a transgenic non-human animal that recombinantly expresses miR-29, which can be produced according to methods well-known in the art. The transgenic non-human animal can be from any species, including avians and non-human mammals. According to this aspect of the invention, suitable non-human mammals include mice, rats, rabbits, guinea pigs, goats, sheep, pigs, and cattle. Suitable avians include chickens, ducks, geese, quail, turkeys, and pheasants.

The polynucleotide encoding miR-29 can be stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells comprise and express the polynucleotide encoding miR-29 so that the animal is a useful screening tool.

Exemplary methods of using the transgenic non-human animals of the invention for in vivo screening of compounds that modulate the level of miR-29 and/or apoptosis comprise administering a test compound to a transgenic non-human animal (e.g., a mammal such as a mouse) comprising an isolated polynucleotide encoding miR-29 stably incorporated into the genome and detecting whether the test compound modulates miR-29 levels and/or apoptosis.

It is known in the art how to measure these responses in vivo. Illustrative approaches include observation of changes that can be studied by gross examination, histopathology, cell markers, and enzymatic activity.

The transgenic non-human animals of the invention also can be used to study the process of apoptosis and the effect of miR-29 on disorders associated with apoptosis. Animals that overexpress miR-29 or do not express miR-29 can be created. These transgenic animals can be exposed to apoptotic signals and the response of cells can be observed. In another example, the transgenic animal can be crossed with animal models of disorders associated with apoptosis, such as epilepsy or neurodegenerative disease, to observe the effect of miR-29 expression or loss of miR-29 expression on the disorder.

Methods of making transgenic animals are known in the art. DNA or RNA constructs can be introduced into the germ line of an avian or mammal to make a transgenic animal. For example, one or several copies of the construct can be incorporated into the genome of an embryo by standard transgenic techniques.

In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the transgene into the embryo can be accomplished by any of a variety of means known in the art such as microinjection, electroporation, lipofection, or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct by Southern blot analysis of a segment of tissue. An embryo having one or more copies of the exogenous cloned construct stably integrated into the genome can be used to establish a permanent transgenic animal line.

Transgenically altered animals can be assayed after birth for the incorporation of the construct into the genome of the offspring. This can be done by hybridizing a probe corresponding to the polynucleotide sequence coding for the polypeptide or a segment thereof onto chromosomal material from the progeny. Those progeny found to contain at least one copy of the construct in their genome are grown to maturity.

Methods of producing transgenic avians are also known in the art, see, e.g., U.S. Pat. No. 5,162,215.

In particular embodiments, to create an animal model in which the expression of miR-29 is decreased, it is desirable to inactivate, replace or knock-out the endogenous gene encoding miR-29 by homologous recombination with a transgene using embryonic stem cells. In this context, a transgene is meant to refer to heterologous nucleic acid that upon insertion within or adjacent to the gene results in a decrease or inactivation of gene expression.

A knock-out of a gene means an alteration in the sequence of a gene that results in a decrease of function of the gene, preferably such that the gene expression is undetectable or insignificant. Knock-outs as used herein also include conditional knock-outs, where alteration of the gene can occur upon, for example, exposure of the animal to a substance that promotes gene alteration (e.g., tetracycline or ecdysone), introduction of an enzyme that promotes recombination at a gene site (e.g., Cre in the Cre-lox system), or other method for directing the gene alteration postnatally. Knock-out animals may be prepared using methods known to those of skill in the art. See, for example, Hogan, et al. (1986) Manipulating the Mouse Embryo: A Laboratory Manual, Cold Spring Harbor Laboratory Press, Cold Spring Harbor, N.Y.

A knock-out construct is a nucleic acid sequence, such as a DNA or RNA construct, which, when introduced into a cell, results in suppression (partial or complete) of expression of a microRNA encoded by endogenous DNA in the cell. A knock-out construct as used herein may include a construct containing a first fragment from the 5' end of the gene encoding miR-29, a second fragment from the 3' end of the gene and a DNA fragment encoding a selectable marker positioned between the first and second fragments. It should be understood by the skilled artisan that any suitable 5' and 3' fragments of a gene may be used as long as the expression of the corresponding gene is partially or completely suppressed by insertion of the transgene. Suitable selectable markers include, but are not limited to, neomycin, puromycin and hygromycin. In addition, the construct may contain a marker, such as diphtheria toxin A or thymidine kinase, for increasing the frequency of obtaining correctly targeted cells. Suitable vectors include, but are not limited to, pBLUESCRIPT, pBR322, and pGEM7.

Alternatively, a knock-out construct may contain RNA molecules such as antisense RNA, siRNA, and the like to decrease the expression of miR-29. Typically, for stable expression the RNA molecule is placed under the control of a promoter. The promoter may be regulated, if deficiencies in miR-29 may lead to a lethal phenotype, or the promoter may drive constitutive expression of the RNA molecule such that the gene of interest is silenced under all conditions of growth. While homologous recombination between the knock-out construct and the gene of interest may not be necessary when using an RNA molecule to decrease gene expression, it may be advantageous to target the knock-out construct to a particular location in the genome of the host organism so that unintended phenotypes are not generated by random insertion of the knock-out construct.

The knock-out construct may subsequently be incorporated into a viral or nonviral vector for delivery to the host animal or may be introduced into embryonic stem (ES) cells. ES cells are typically selected for their ability to integrate into and become part of the germ line of a developing embryo so as to create germ line transmission of the knock-out construct. Thus, any ES cell line that can do so is suitable for use herein. Suitable cell lines which may be used include, but are not limited to, the 129J ES cell line or the J1 ES cell line. The cells are cultured and prepared for DNA insertion using methods well-known to the skilled artisan (e.g., see Robertson (1987) In: Teratocarcinomas and Embryonic Stem Cells: A Practical Approach, E. J. Robertson, ed. IRL Press, Washington, D.C.; Bradley et al., Curr. Topics Develop. Biol. 20:357 (1986); Hogan et al., (1986) Manipulating the Mouse Embryo: A Laboratory Manual, Cold Spring Harbor Laboratory Press, Cold Spring Harbor, N.Y.).

Insertion of the knock-out construct into the ES cells may be accomplished using a variety of methods well-known in the art, including, for example, electroporation, microinjection, and calcium phosphate treatment. For insertion of the DNA or RNA sequence, the knock-out construct nucleic acids are added to the ES cells under appropriate conditions for the insertion method chosen. If the cells are to be electroporated, the ES cells and construct nucleic acids are exposed to an electric pulse using an electroporation machine (electroporator) and following the manufacturer's guidelines for use. After electroporation, the cells are allowed to recover under suitable incubation conditions. The cells are then screened for the presence of the knockout construct.

Each knock-out construct to be introduced into the cell is first typically linearized if the knock-out construct has been inserted into a vector. Linearization is accomplished by digesting the knock-out construct with a suitable restriction endonuclease selected to cut only within the vector sequence and not within the knock-out construct sequence.

Screening for cells which contain the knock-out construct (homologous recombinants) may be done using a variety of methods. For example, as described herein, cells can be processed as needed to render DNA in them available for hybridization with a nucleic acid probe designed to hybridize only to cells containing the construct. For example, cellular DNA can be probed with $^{32}$P-labeled DNA which locates outside the targeting fragment. This technique can be used to identify those cells with proper integration of the knock-out construct. The DNA can be extracted from the cells using standard methods (e.g., see, Sambrook et al., Molecular Cloning: A Laboratory Manual 2nd Ed. (Cold Spring Harbor, N.Y., 1989)). The DNA may then be analyzed by Southern blot with a probe or probes designed to hybridize in a specific pattern to genomic DNA digested with one or more particular restriction enzymes.

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Germline transmission of the knockout construct may be determined using standard methods. Offspring resulting from implantation of embryos containing the ES cells described above are screened for the presence of the desired alteration (e.g., knock-out of miR-29). This may be done, for example, by obtaining DNA from offspring (e.g., tail DNA) to assess for the knock-out construct, using known methods (e.g., Southern analysis, dot blot analysis, PCR analysis). See, for example, Sambrook et al., Molecular Cloning: A Laboratory Manual 2nd Ed. (Cold Spring Harbor, N.Y., 1989). Offspring identified as chimeras may be crossed with one another to produce homozygous knock-out animals.

Mice are often used as animal models because they are easy to house, relatively inexpensive, and easy to breed. However, other knock-out animals may also be made in accordance with the present invention such as, but not limited to, monkeys, cattle, sheep, pigs, goats, horses, dogs, cats, guinea pigs, rabbits and rats. Accordingly, appropriate vectors and promoters well-known in the art may be selected and used to generate a transgenic animal that overexpresses or is deficient in expression of miR-29.

The present invention is more particularly described in the following examples that are intended as illustrative only since numerous modifications and variations therein will be apparent to those skilled in the art.

EXAMPLE 1

Experimental Methods

Cell Culture.

Primary sympathetic neurons were cultured as described previously (Potts et al., *J. Cell Biol.* 163:789 (2003)). Briefly, superior cervical ganglia of P0 mice were dissected and treated for 30 min at 37° C. each with 1 mg/mL collagenase followed by 2.5 mg/mL trypsin (both from Worthington Biochemical Corporation). Cells were plated on collagen coated dishes in NGF-containing media before treatments. To obtain P5 or P28 neurons, P0 neurons were maintained in culture for either 5 days or 28 days, respectively. NGF deprivation was performed by washing cultures three times with medium lacking NGF followed by maintenance of cells in NGF-lacking media containing anti-NGF neutralizing antibodies. For DNA damage- and ER stress-inducing treatments, cells were treated with 20 μM etoposide (Sigma) or 2.5 μM tunicamycin (Sigma), respectively. For luciferase assay experiments, HEK-293T cells were grown in medium containing DMEM/F12 (Gibco), supplemented with 10% FBS, 100 U/ml penicillin, and 100 μg/ml streptomycin.

MicroRNA Extraction and Microarray Analysis.

For miRNA microarray and real-time PCR analysis, total RNA was extracted using Trizol Reagent (Invitrogen) or the miRNeasy kit (Qiagen). miRNA microarray was performed essentially as previously described (Thomson et al., *Nat. Methods* 1:47 (2004)). Briefly, 8 μg RNA was extracted from superior cervical sympathetic ganglia of E18, P5, P13, and P28 mice and was ligated with a Cy3-labeled dinucleotide (5' phosphate-cytidyl-uridyl-Cy3-3') using RNA ligase and labeled RNA was hybridized to the microarray. Normalized $\log_2$ data were hierarchically clustered by sample and represented as a heat map using Cluster 3.0 and TreeView software programs, respectively (Michael Eisen, Stanford University).

Real-Time PCR Analysis.

Mature miR-29b expression was assayed using TaqMan MicroRNA Assays (Applied Biosystems). Briefly, 10 ng of RNA was reverse transcribed using Superscript II reverse transcriptase (Invitrogen) and specific RT primers for either miR-29a, miR-29b, miR-29c, or U6 RNA (Applied Biosystems). cDNA was amplified in an ABI7500 system using TaqMan Universal PCR Master Mix (Applied Biosystems). miR-29b and U6 RNA primers and TaqMan probes were designed by Applied Biosystems and provided in the respective MicroRNA Assay kit. Relative quantification was carried out using the delta-delta Ct method. Sample variability was corrected by normalizing to U6 RNA levels.

Microinjection and Quantification of Cell Survival.

Cells were injected with 30 μM miR-29b or a control *C. elegans* miRNA (cel-miR-67) that is not conserved in mammalian cells (miRIDIAN mimics; Dharmacon) along with rhodamine dextran (8 μg/μl) and EGFP-expressing plasmid (50 ng/μL) in microinjection buffer containing 100 mM KCl and 10 mM KPi, pH 7.4 as described previously (Potts et al., *J. Cell Biol.* 163:789 (2003)). This concentration of miR-29b was estimated to elevate miR-29b to approximately the levels seen in P28 neurons. To determine the concentration of miR-29b after microinjection into P5 neurons, we first quantified the absolute concentration of miR-29b in P5 neurons. qRT-PCR for miR-29b on a known number of culture P5 neurons was compared to a standard curve of PCR-amplified pure miR-29b. Using these findings and assuming a volume of 8 fL per neuron (based on a 20 nm soma diameter plus approximate axonal volume), we estimated the concentration of miR-29b to be 220 nM in P5 neurons. Thus P28 neurons, which we find express ~12-fold higher levels of miR-29b than P5 neurons (FIG. 1C), contain approximately 2.6 μM miR-29b. We estimate that we inject an amount of miR-29b corresponding to ~10% of the volume of the cell (Deshmukh et al., *Neuron* 21:695 (1998). Based on these calculations, injection of 30 μM miR-29b results in a final concentration of about 3 μM into P5 neurons, which is approximately the concentration in P28 neurons. The number of viable rhodamine-positive cells with intact phase-bright cell bodies was counted prior to treatment with NGF deprivation, etoposide, or tunicamycin and then counted at indicated times after cell treatment. Cell survival was expressed as a percentage of the number of cells prior to treatment (time 0). This method of assessing survival has correlated well with other cell survival assays such as trypan blue exclusion, calcein AM staining, and follows recent guidelines for assessment of death in neuronal cells (Potts et al., *J. Cell Biol.* 163:789 (2003); Galluzzi et al., *Cell Death Differ.* 16:1093 (2009)).

Cloning of pCAG-miR-29b-GFP.

A 198 by fragment of the miR-29b precursor was PCR amplified from wild-type mouse DNA (primers listed in Table 1) and cloned into a modified splice-donor/splice-acceptor vector (Newman et al., *RNA* 14:1539 (2008)) containing the CMV early enhancer/chicken β-actin (CAG) promoter.

Immunofluorescence Staining.

Immunofluorescence staining was performed as previously described (Potts et al., *J. Cell Biol.* 163:789 (2003)). Briefly, neurons were fixed for 30 min in 4% paraformaldehyde and blocked for 1 hr at room temperature in a solution containing Tris-buffered saline, 5% donkey serum, and 0.3% Triton-X-100. Neurons were then incubated overnight in the same blocking solution containing the following primary antibodies: anti-cytochrome c (#556432, BD Biosciences; 1:400 dilution), anti-phospho-c-Jun-Ser63 (#9261, Cell Signaling; 1:1000 dilution), or anti-Bim (#2819, Cell Signaling; 1:2000 dilution). Incubations with secondary antibodies were performed for 1 hr at room temperature with either anti-mouse Cy3-conjugated or anti-rabbit Cy3-conjugated antibodies (Jackson Immunoresearch Laboratories Inc.; 1:400 dilution). Nuclei were stained with Hoechst 33258 (Molecular Probes). For staining of NGF-deprived neurons, NGF deprivation was done in the presence of 25 μM Q-VD-OPh (MP Biomedicals) to prevent caspase activation and apoptosis.

Cloning of BH3-Only 3' UTRs for Luciferase Activity Assays.

3'UTR segments of several BH3-only genes containing putative miR-29b binding sites were cloned into the pGL3-control plasmid (Promega) which had been modified to place the multiple cloning site downstream of the firefly luciferase gene (a kind gift from Dr. Da-Zhi Wang, Children's Hospital Boston, Boston, Mass.). Bim, Bmf, Hrk, and N-Bak 3'UTR segments were amplified from wild-type mouse DNA using primers containing SacI, MluI, or XhoI sites. For Puma, oligonucleotides containing sense and antisense sequences of a portion of the wild-type or mutant Puma 3' UTR were annealed and ligated directly into pGL3. For all other constructs, 8-nucleotide deletions in the seed region of the miR-29b binding site were generated following the QuikChange II Site-Directed Mutagenesis (Agilent) manufacturer instructions. All oligonucleotide sequences used are listed in Table 1.

TABLE 1

| Gene | Forward | Reverse |
|---|---|---|
| PCR amplification of BH3-only gene 3'UTRs | | |
| Bim | TCGAGCTCCTACATGCAGCCAGGATACG (SEQ ID NO: 11) | CGCTCGAGAAGAGAAAAGCCCTCCCTTG (SEQ ID NO: 12) |
| Bmf | TCACGCGTTTCAGCTAGGCCAGAAAGGA (SEQ ID NO: 13) | CGCTCGAGGGGAAGCCATCTTTCTTTGA (SEQ ID NO: 14) |
| Hrk | TCGAGCTCTGTGGAGTAGAGGGGACTGG (SEQ ID NO: 15) | CGCTCGAGAGACTCTGGCCGTACCAAGA (SEQ ID NO: 16) |
| N-Bak | TCGAGCTCGCCTGGCTGGACTAAACCTC (SEQ ID NO: 17) | CGCTCGAGAGGAGTGTTGGGAACACAGG (SEQ ID NO: 18) |

| Gene | Sense | Antisense |
|---|---|---|
| Mutagenesis of BH3-only gene 3'UTRs | | |
| Bim | CCACGCGTCATGTCCCTCTCTCGACAGTGTGT (SEQ ID NO: 19) | ACACACTGTCGAGAGAGGGACATGACGCGTGG (SEQ ID NO: 20) |
| Bmf | GTTATGTATGTAAGGAAAGACATTAATGAAGATGAGCCAAGGCTCA (SEQ ID NO: 21) | TGAGCCTTGGCTCATCTTCATTAATGTCTTTCCTTACATACATAAC (SEQ ID NO: 22) |
| Hrk site 1 | CCTTACCTATATAGTGTGTCTCACTTCACAGTTTCTTGGT (SEQ ID NO: 23) | ACCAAGAAACTGTGAAGTGAGACACACTATATAGGTAAGG (SEQ ID NO: 24) |
| Hrk site 2 | TGTCTCACTTCACAGTTTCTAAGTGTATCCTTCTTGGTAC (SEQ ID NO: 25) | GTACCAAGAAGGATACACTTAGAAACTGTGAAGTGAGACA (SEQ ID NO: 26) |
| N-Bak | AATACCCCAACATTGCACTGAACCCCATCCTGTC (SEQ ID NO: 27) | GACAGGATGGGGTTCAGTGCAATGTTGGGGTATT (SEQ ID NO: 28) |
| Cloning of Puma 3'UTRs | | |
| Puma wt | CGCGTGGGTGTCCCCAGTGCGCCTTCACTTTGGGCCTGGCCTCAGGCCCCTGGTGCTTC (SEQ ID NO: 29) | TCGAGAAGCACCAGGGGCCTGAGGCCAGGCCCAAAGTGAAGGCGCACTGGGGACACCCA (SEQ ID NO: 30) |
| Puma mutant | CGCGTGGGTGTCCCCAGTGCGCCTTCACTTTGGGCCTGGCCTCAGGCCCCC (SEQ ID NO: 31) | TCGAGGGGCCTGAGGCCAGGCCCAAAGTGAAGGCGCACTGGGGACACCCA (SEQ ID NO: 32) |

| Gene | Forward | Reverse |
|---|---|---|
| qRT-PCR of BH3-only mRNAs | | |
| Bim | CAAGTCAACACAAACCCCAAGTC (SEQ ID NO: 33) | GTCGTATGGAAGCCATTGCA (SEQ ID NO: 34) |
| Puma | AGCGGCGGAGACAAGAAGA (SEQ ID NO: 35) | AGTCCCATGAAGAGATTGTACATGAC (SEQ ID NO: 36) |
| Gapdh | TGTGTCCGTCGTGGATCTGA (SEQ ID NO: 37) | CCTGCTTCACCACCTTCTTGA (SEQ ID NO: 38) |
| PCR Amplification of miR-29b-1 for pCAG-miR-29b-1-GFP | | |
| | GTCTCGAGGCCACAAAAACAGACGACAA (SEQ ID NO: 39) | GCGAATTCAGGGCAGGCTCTGGTAGC (SEQ ID NO: 40) |

Luciferase Activity Assays.

Luciferase assays were performed in HEK-293T cells by plating approximately 60,000 cells into each well of a 12-well plate. For transfections, 1.5 μg of each pGL3-3'UTR construct was co-transfected with 100 ng phRL renilla luciferase (Promega) and 20 nM of miR-29b or cel-miR-67 miRIDIAN mimics (Dharmacon), Transfections were performed using Lipofectamine-2000 (Invitrogen) according to the manufacturer's instructions. Lysates were collected 48 hrs after transfection, and both renilla and firefly luciferase activities were measured with a Dual-Luciferase Reporter System (Promega) according to the manufacturer's instructions, using a Fluoroskan plate reader (ThermoLabSystems). Firefly-to-renilla luciferase ratios were calculated for each sample to normalize for cell number and transfection efficiency.

Western Blot.

blots were performed as described previously (Potts et al., J. Cell Biol. 163:789 (2003)). Primary antibodies for immunoblotting were as follows: anti-Bim (Stressgen; 1:1,000 dilution), anti-Bmf (17A9, Alexis Biochemicals; 1:1,000 dilution), anti-Puma (#4976, Cell Signaling; 1:1,000 dilution), anti-Mcl-1 (Rockland Immunochemicals; 1:1,000 dilution), and anti-alpha tubulin (Sigma; 1:10,000 dilution). HRP conjugated secondary antibodies were purchased from Pierce Chemical Co. Western blots were developed using the ECL-Plus detection system (Amersham Biosciences). Densitometric analysis was performed using ImageJ software (NIH).

cDNA Synthesis and qRT-PCR Analysis.

For analysis of BH3-only mRNAs, cDNA was synthesized using 150-300 ng RNA. RNA samples were first treated with RQ1 DNase (Promega) for 30 min at 37° C. followed by a 10 min incubation at 65° C. with DNase Stop Solution (Promega). DNase-treated RNA was mixed with 0.25 μg random hexamer primers (Invitrogen) and reverse transcribed using Superscript II reverse transcriptase (Invitrogen) according to the manufacturer's instructions. Each 25 μL PCR reaction contained 1 μL cDNA, each primer at a final concentration of 400 nM, and Power SYBR Green PCT Master Mix (Applied Biosystems). Primers were designed using Primer Express software (Applied Biosystems; sequences in Supplementary Table S2). Reactions were amplified in an ABI7500 system and relative quantification was carried out using the delta-delta Ct method. Sample variability was corrected by normalizing to GAPDH levels.

Image Acquisition and Processing.

Images were acquired by an ORCA-ER digital B/W CCD camera (Hamamatsu) mounted on a DMIRE2 inverted fluorescence microscope (Leica). The image acquisition software was Metamorph version 7.6 (Molecular Devices). Images were scaled down and cropped in Adobe Photoshop to prepare the final figures.

Statistics.

P-values were calculated using an unpaired, two-tailed, Student's t-test.

EXAMPLE 2

Identification of miRNA Involved in Regulation of Apoptosis

In contrast to developing P5 (post-natal day 5) sympathetic neurons, mature P28 neurons are strikingly resistant to NGF deprivation and the DNA-damaging agent etoposide (FIG. 1A) (Wright et al., *J. Cell Biol.* 179:825 (2007); Easton et al., *J. Neurosci.* 17:9656 (1997)). To determine whether miRNAs may have a role in restricting apoptosis, we profiled their expression during neuronal maturation and reasoned that miRNAs which are most highly expressed in mature neurons would likely function to prevent cell death. Sympathetic neurons were obtained from the superior cervical ganglia (SCG) of mice at four developmental stages: embryonic day 18 (E18), P5, P13, and P28. Each of these stages occur after post-mitotic differentiation, thereby focusing our study on a time period when increasing restriction of apoptosis is a known event occurring in these neurons (Glebova et al., *Annu. Rev. Neurosci.* 28:191 (2005)). Using Significance Analysis of Microarrays (SAM) (Tusher et al., *Proc. Natl. Acad. Sci. USA* 98:5116 (2001)) to compare young (E18, P5) to mature (P13, P28) neurons, we found that the expression of only one miRNA family, miRNA-29 (miR-29), was significantly increased in mature neurons (FIG. 1B).

Figure 2:
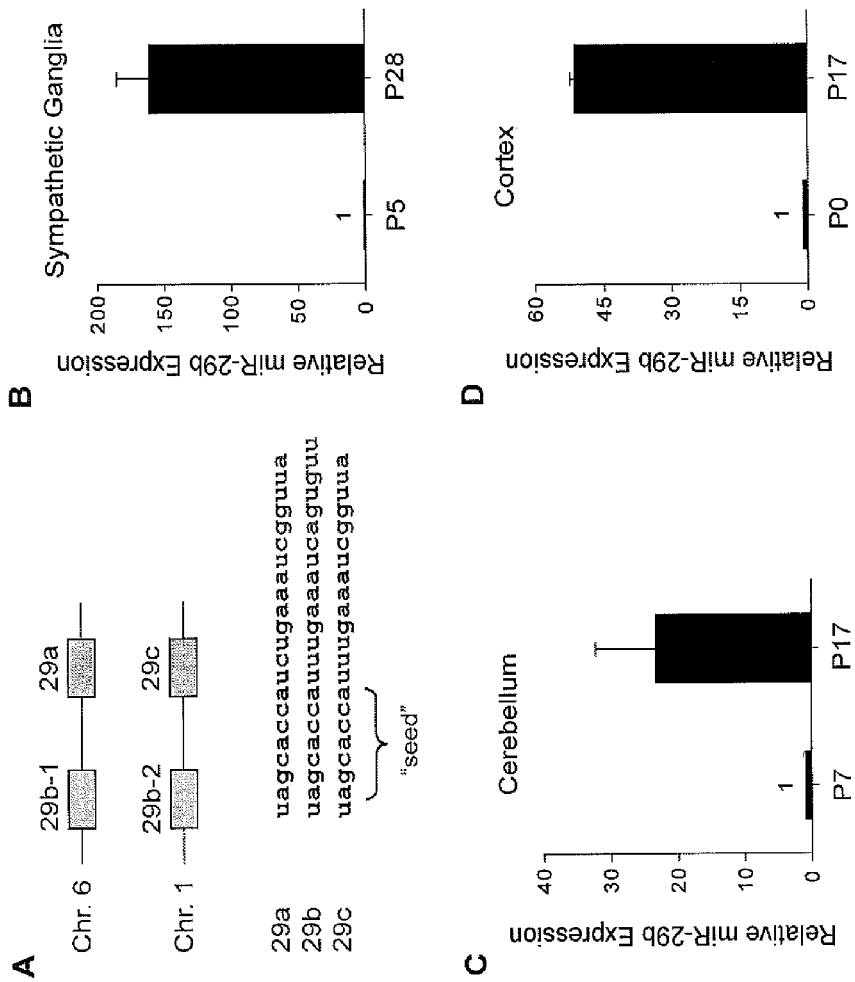
FIGS. 2A-2D show expression of miR-29b is increased during maturation of several regions of the nervous system. A) Schematic representation of the genomic organization of the mouse miR-29 loci and alignment of mature miR-29a, miR-29b, and miR-29c sequences (SEQ ID NOS:1-3). Non-conserved nucleotides are indicated in gray. B-D) qRT-PCR for miR-29b using RNA collected from (B) sympathetic ganglia of P5 and P28 mice, (C) cerebellum of P7 and P17 mice, and (D) cortex of P0 and P17 mice, miR-29b expression is plotted relative to levels in P5 sympathetic ganglia, P7 cerebellum, and P0 cortex, respectively. Data in (B-D) are mean±s.e.m. of three independent experiments.

The miR-29 family consists of three members (miR-29a, miR-29b, and miR-29c) that map to two distinct genomic loci in clusters. Since these miRNAs have extensive sequence homology, especially at the 5' seed region important for mRNA target recognition (Lewis et al., *Cell* 115:787 (2003)), we focused on miR-29b as it is expressed from both genomic loci (FIG. 2A). To confirm our microarray data, we performed quantitative RT-PCR (qRT-PCR) on isolated ganglia from P5 and P28 mice and found the levels of miR-29b to be increased over 100-fold in P28 ganglia (FIG. 2B). In addition, using pure neuronal cultures, miR-29b levels increased in P0 neurons cultured for 28 days in vitro (P28-equivalent) versus neurons cultured for 5 days (P5-equivalent) (FIG. 1C), indicating that the increase in miR-29b occurs specifically in neurons. The increase in miR-29b with neuronal maturation was not specific to sympathetic neurons as a similar increase in expression was also observed during cerebellar and cortical maturation (FIGS. 2C and 2D). Together, these data indicate that miR-29b levels are induced at a time when neurons become increasingly resistant to apoptosis.

Figure 3:
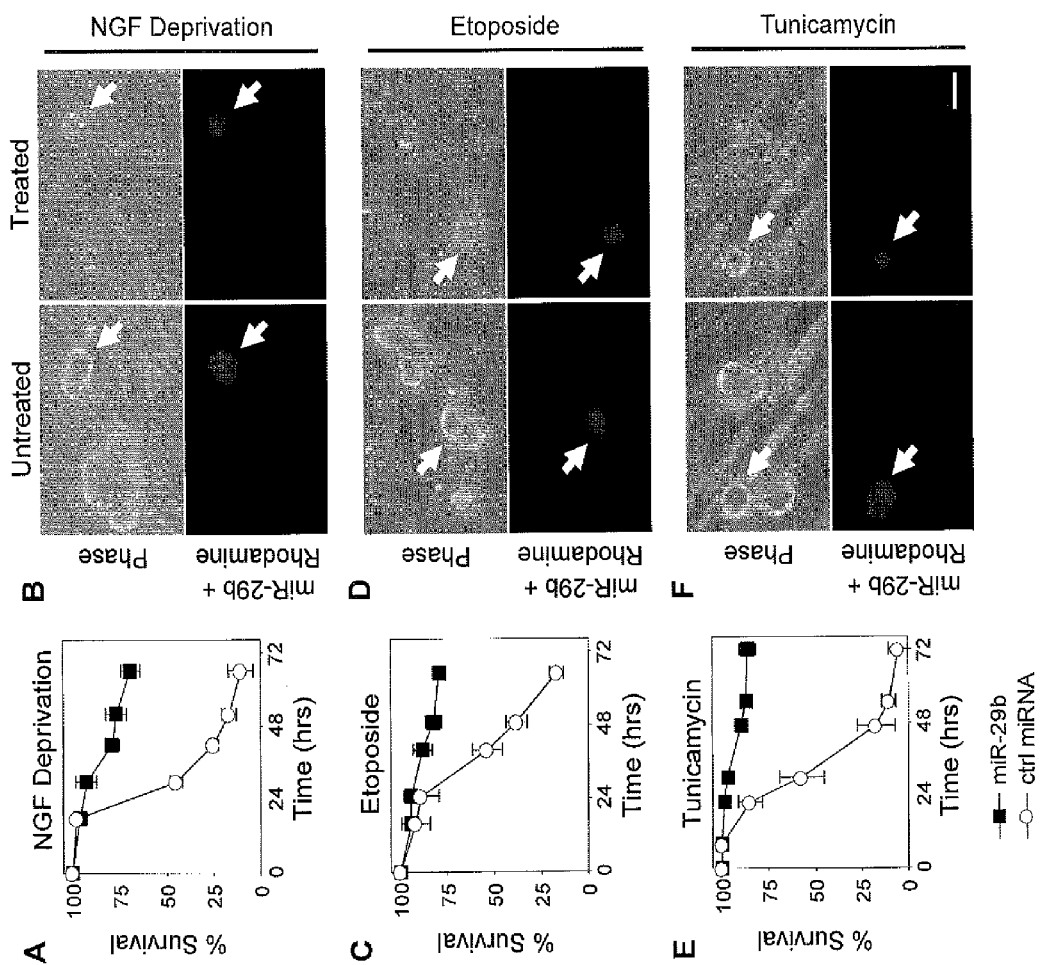
FIGS. 3A-3F show miR-29b expression potently inhibits neuronal apoptosis induced by multiple stimuli. P3 sympathetic neurons were microinjected with miR-29b or cel-miR-67 (ctrl miRNA, each 30μM) together with rhodamine to mark injected cells. (A, C, E) 48 hrs following injection, neurons were subjected to (A) NGF deprivation, (C) 20 μM etoposide, or (E) 2.5 μM tunicamycin, and survival of injected cells was assessed at various time points following cell treatment. Survival was expressed as a percentage of viable cells prior to treatment. (B, D, F) Representative phase-contrast images of the exact field of sympathetic neurons before (untreated) or after 3 days of (B) NGF deprivation, (D) etoposide), or (F) tunicamycin. Rhodamine marks cells injected with 30 μM miR-29b (arrows). d) Representative phase-contrast images of the exact field of sympathetic neurons before (untreated) or after 3 days of etoposide treatment (20 μM). Rhodamine marks cells injected with 30 μM miR-29b (arrows). Data in A, C, and E are mean±s.d. of at least three independent experiments. Bar, 20 μm.
Figure 4:
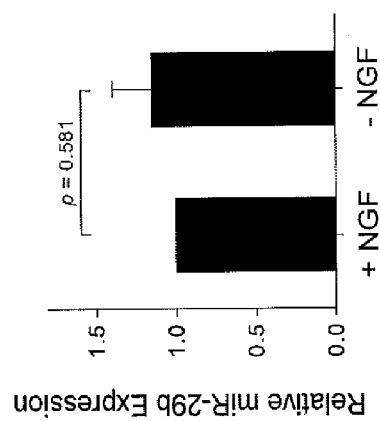
FIG. 4 shows expression of miR-29b is unaffected by NGF deprivation in P5 neurons. qRT-PCR of P5 sympathetic neurons which were either maintained in NGF-containing media (+NGF) or deprived of NGF (−NGF) for 48 hrs. miR-29b expression is plotted relative to levels in neurons maintained in NGF. Data are mean±s.e.m. of at least three independent experiments.

Since the marked increase in miR-29 expression during maturation correlates with a time when strict restrictions on neuronal apoptosis are engaged, we hypothesized that introducing miR-29b in young P5 neurons may provide enhanced resistance to apoptotic stimuli. miR-29b or a control miRNA (non-conserved *C. elegans* miRNA, cel-miR-67) were microinjected into P3 neurons and after 48 hours, neurons were subjected to NGF deprivation. Remarkably, microinjection of miR-29b was sufficient to protect neurons from apoptosis, while cells injected with the control miRNA died at the expected rate (FIGS. 3A and 3B). Treatment of P5 neurons with NGF deprivation alone did not have a significant effect on the endogenous expression of miR-29b (FIG. 4). The ability of miR-29b to inhibit neuronal apoptosis was not specific to NGF deprivation as miR-29b expression also effectively inhibited apoptosis in response to DNA damage (FIGS. 3C and 3D) and ER stress (FIGS. 3E and 3F). These data indicate that miR-29b is a potent inhibitor of neuronal apoptosis induced by multiple stimuli.

EXAMPLE 3

Regulation of BH3-Only Proteins by miR-29b

Figure 5:
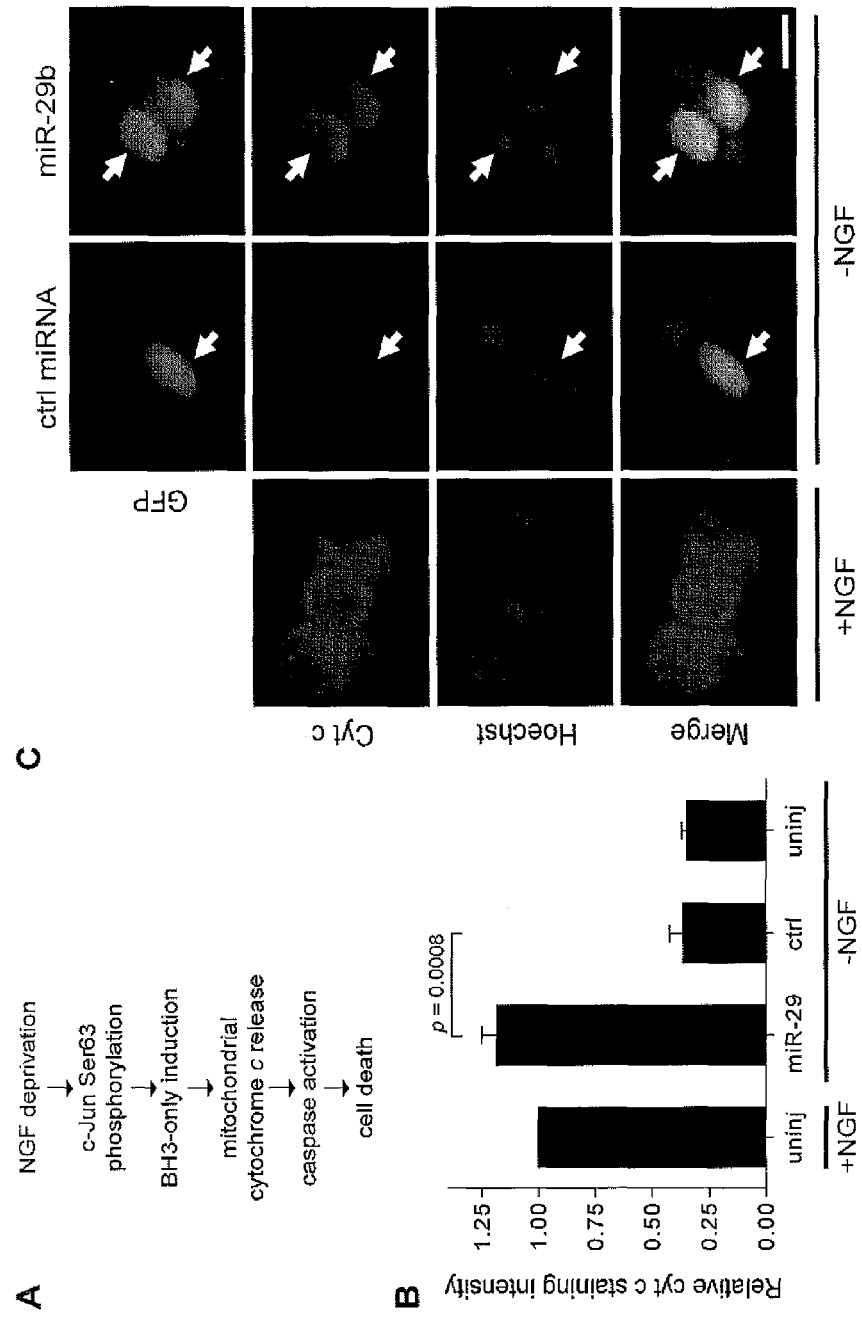
FIGS. 5A-5C show inhibition of apoptosis by miR-29b occurs upstream of cytochrome c release. A) Schematic representation of the apoptosis pathway activated after NGF deprivation in P5 neurons. (B, C) P3 sympathetic neurons were either uninjected (uninj) or microinjected with a GFP-expressing plasmid and either miR-29b or cel-miR-67 (ctrl miRNA, each 30 μM). After 48 hrs, cells were left untreated (+NGF) or deprived of NGF (−NGF). Cells were fixed and immunostained 48 hrs after cell treatment. B) Fluorescence intensity of cells after cytochrome c staining. C) Representative photographs of cytochrome c staining in neurons; GFP expression indicates injected cells (arrows). Data in (B) are mean±s.e.m. of at least three independent experiments. Bar, 20 μm.
Figure 6:
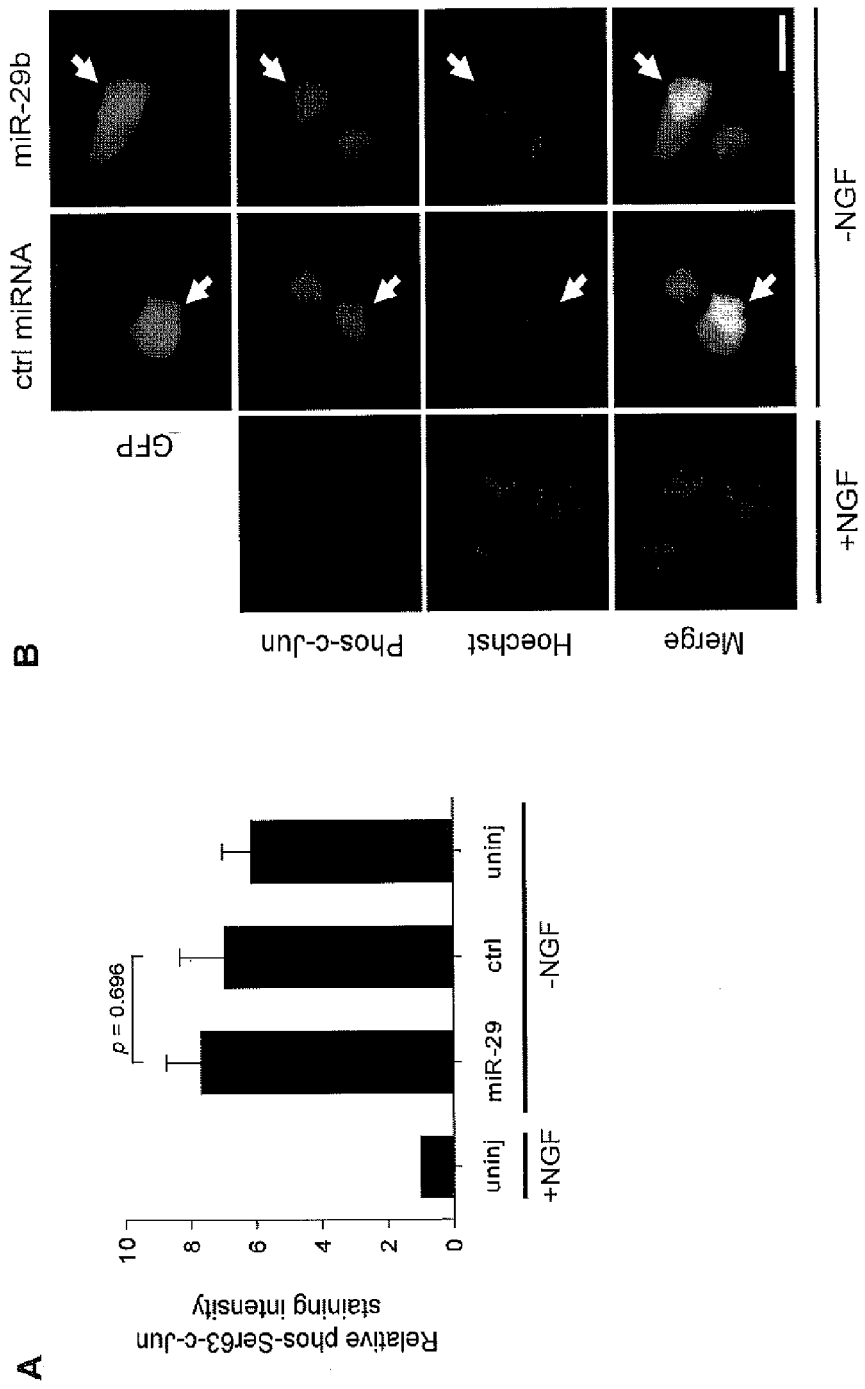
FIGS. 6A-6B show inhibition of apoptosis by miR-29b occurs downstream of c-Jun phosphorylation. A, B) P3 sympathetic neurons were either uninjected (uninj), or microinjected with a GFP-expressing plasmid and either miR-29b or cel-miR-67 (ctrl miRNA, each 30 μM). After 48 hrs, cells were left untreated (+NGF) or deprived of NOF (−NGF). Cells were fixed and immunostained 48 hrs after cell treatment. A) Fluorescence intensity of cells after phospho-Ser63-c-Jun staining. B) Representative photographs of phospho-Ser63-c-Jun staining in neurons; GFP expression indicates injected cells (arrows). Data in (A) are mean±s.e.m. of three independent experiments. Scale bar, 10 μm.
Figure 7:
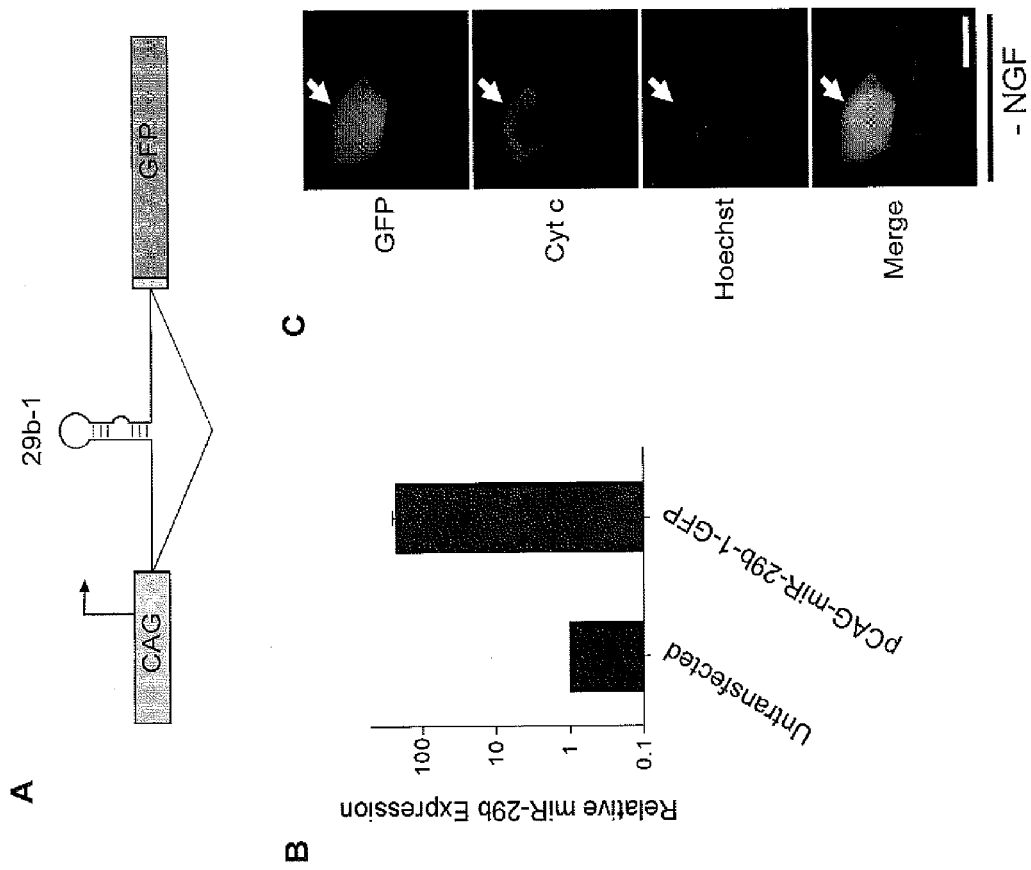
FIGS. 7A-7C show cytochrome c release is blocked by miR-29b-1 expression after NGF deprivation in neurons. A) Schematic representation of a construct generated for expression of miR-29b-1 and GFP under control of the CMV early enhancer/chicken β-actin (CAG) promoter (pCAG-miR-29b-1-GFP). B) Expression of miR-29b in HEK 293T cells was measured by qRT-PCT. RNA was collected either from HEK 293T cells alone (untransfected) or from HEK 293T cells transfected with miR-29b-1-expressing plasmid (pCAG-miR-29b-1-GFP). C) P3 sympathetic neurons were microinjected with pCAG-miR-29b-1-GFP plasmid (50 ng/μL) and deprived of NGF 48 hrs after injection (−NGF) in the presence of the caspase inhibitor Q-VD-OPh (25 μM) to block cell death. Cells were fixed and stained 2 days after cell treatment. Scale bar, 10 μm.

To determine precisely how miR-29b functions to inhibit apoptosis, we analyzed the effect of miR-29b expression on key steps in the pathway activated by NGF deprivation. Upon NGF withdrawal, neurons activate the transcription factor c-Jun by phosphorylation at serine 63 (Ser63), causing the induction of pro-apoptotic BH3-only proteins in the Bcl-2 family (Eilers et al., *J. Neurosci.* 18:1713 (1998); Whitfield et al., *Neuron* 29:629 (2001)), which results in cytochrome c release, caspase activation, and cell death (FIG. 5A). We examined the phosphorylation status of c-Jun in neurons injected with miR-29b after NGF withdrawal. NGF deprivation induced robust nuclear staining for phospho-Ser63-c-Jun in both control and miR-29b expressing neurons, indicating that miR-29b expression did not affect c-Jun phosphorylation (FIGS. 6A and 6B). Next, we tested the effect of miR-29b on the release of cytochrome c from mitochondria. Following NGF deprivation, while uninjected or control-injected neurons showed very faint cytochrome c staining, consistent with its release to the cytoplasm (Deshmukh et al., *Neuron* 21:695 (1998)), neurons injected with miR-29b maintained cytochrome c. at the mitochondria (FIGS. 5B and 5C; FIGS. 7A-7C). Thus, miR-29b expression potently inhibited apoptosis in neurons downstream of c-Jun phosphorylation but upstream of cytochrome c release. The identification that miR-29b acts at this step in the apoptotic pathway is consistent with the fact that mature neurons, which we have found to express high levels of miR-29, also phosphorylate c-Jun but do not release cytochrome c after NGF deprivation (Putcha et al., *J. Cell Biol.* 149:1011 (2000); Easton et al., *J. Neurosci.* 17:9656 (1997)).

Figure 8:
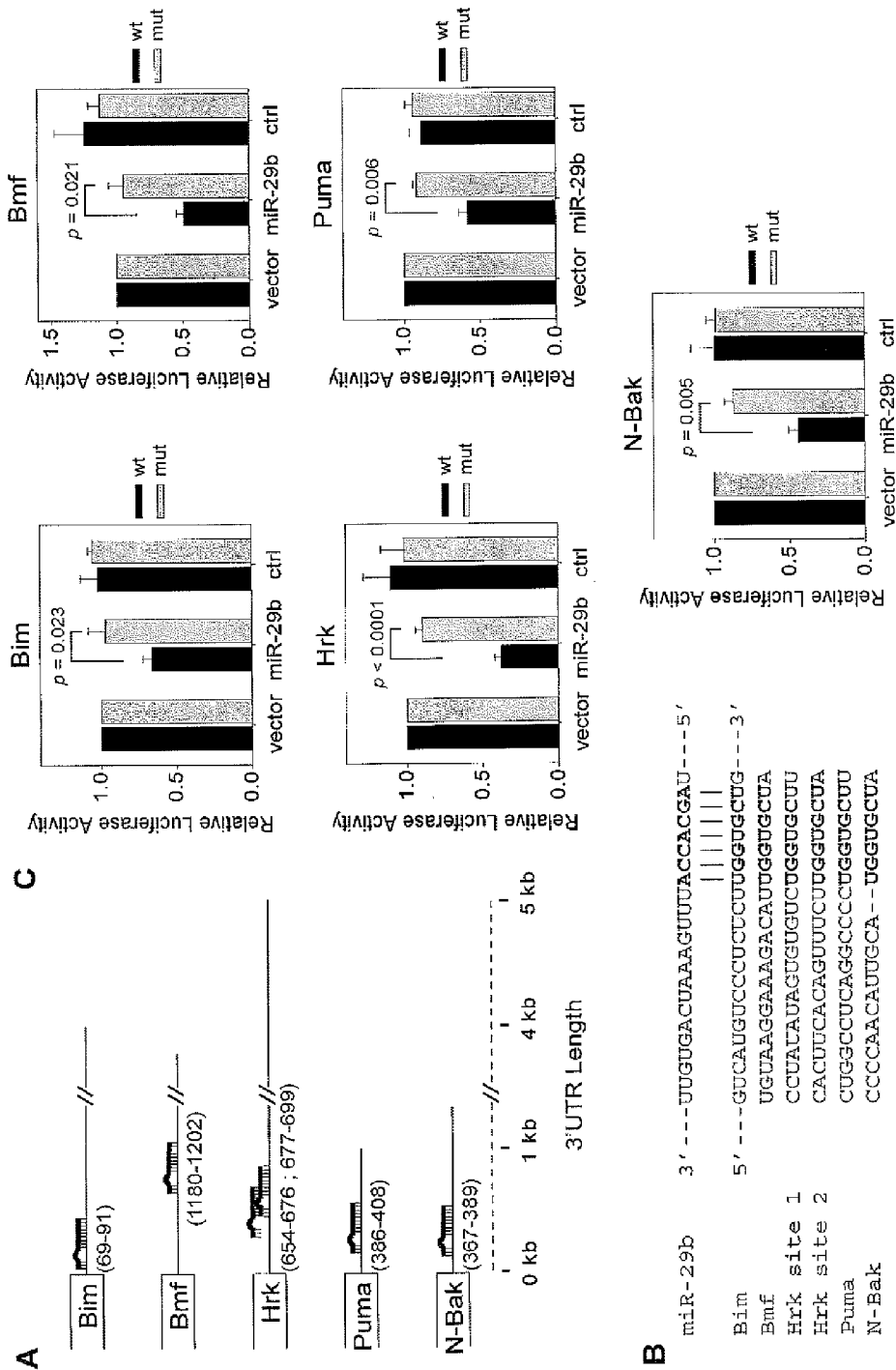
FIGS. 8A-8C show miR-29b targets multiple members of the BH3-only family. A) Schematic representation of predicted miR-29b binding sites in the 3'UTRs of multiple mouse BH3-only mRNAs. Nucleotides of the 3'UTR containing miR-29b binding sites are listed in parentheses. B) Sequence and alignment of the miR-29b binding sites in the 3'UTRs of multiple BH3-only mRNAs (SEQ ID NOS:2 and 4-9). The predicted base pairing of miR-29b with target recognition seed sequence is shown in italic text. C) Luciferase activity was measured 48 hrs after transfection of HEK 293T cells with reporter plasmids in which regions of either wild-type (wt) or mutant (mut) 3'UTRs of genes listed in (A) were each fused downstream from the firefly luciferase gene. Reporter plasmids were either transfected alone (vector), together with 20 nM miR-29b (miR-29b), or together with 20 nM cel-miR-67 (ctrl miRNA). Expression was normalized by taking the ratio of firefly to *renilla* luciferase and is plotted relative to vector alone. Data are mean±s.e.m. of at least three independent experiments.

The BH3-only proteins are a family of pro-apoptotic regulators that are critical for inducing cytochrome c release from mitochondria. This gene family comprises at least eight members, many of which act redundantly (Giam et al., *Oncogene* 27 *Suppl* 1:S128 (2008)). For example, though Bim and Hrk (also known as DP5) are transcriptionally induced and important for NGF deprivation-induced apoptosis, the knock-out of either gene has only a modest effect on survival (Putcha et al., *Neuron* 29:615 (2001); Imaizumi et al., *J. Neurosci.* 24:3721 (2004)). Thus, an effective block of apoptosis at this point would require inhibition of multiple BH3-only proteins. To assess whether miR-29b was capable of functioning in this manner, we used miRNA target prediction programs (TargetScan, microcosm Targets, and PicTar) to determine whether any BH3-only mRNAs were putative targets of miR-29b. To our surprise, we found that multiple BH3-only mRNAs had predicted miR-29b binding sites in their 3'UTRs (FIGS. 8A and 8B).

To directly test whether miR-29b could target BH3-only mRNAs, we used a luciferase reporter assay in which the 3'UTRs of BH3-only genes, with or without the putative miR-29b binding sites, were each fused downstream of the firefly luciferase gene. Each luciferase construct was co-transfected with either miR-29b or a control miRNA into HEK 293T cells and luciferase activity was measured. Indeed, miR-29b was able to effectively reduce luciferase activity in cells transfected with constructs containing 3'UTRs of wild-type, but not mutant, Bim, Bmf, Hrk, and Puma (FIG. 5C). Further, miR-29b was also able to target the 3'UTR of N-Bak, a BH3-only splice variant of Bak which is expressed exclusively in neurons (FIG. 5C) (Ham et al., *Cell Death Differ.* 12:1015 (2005)). Together, these data identify miR-29b as a single molecule capable of targeting multiple BH3-only mRNAs.

Figure 9:
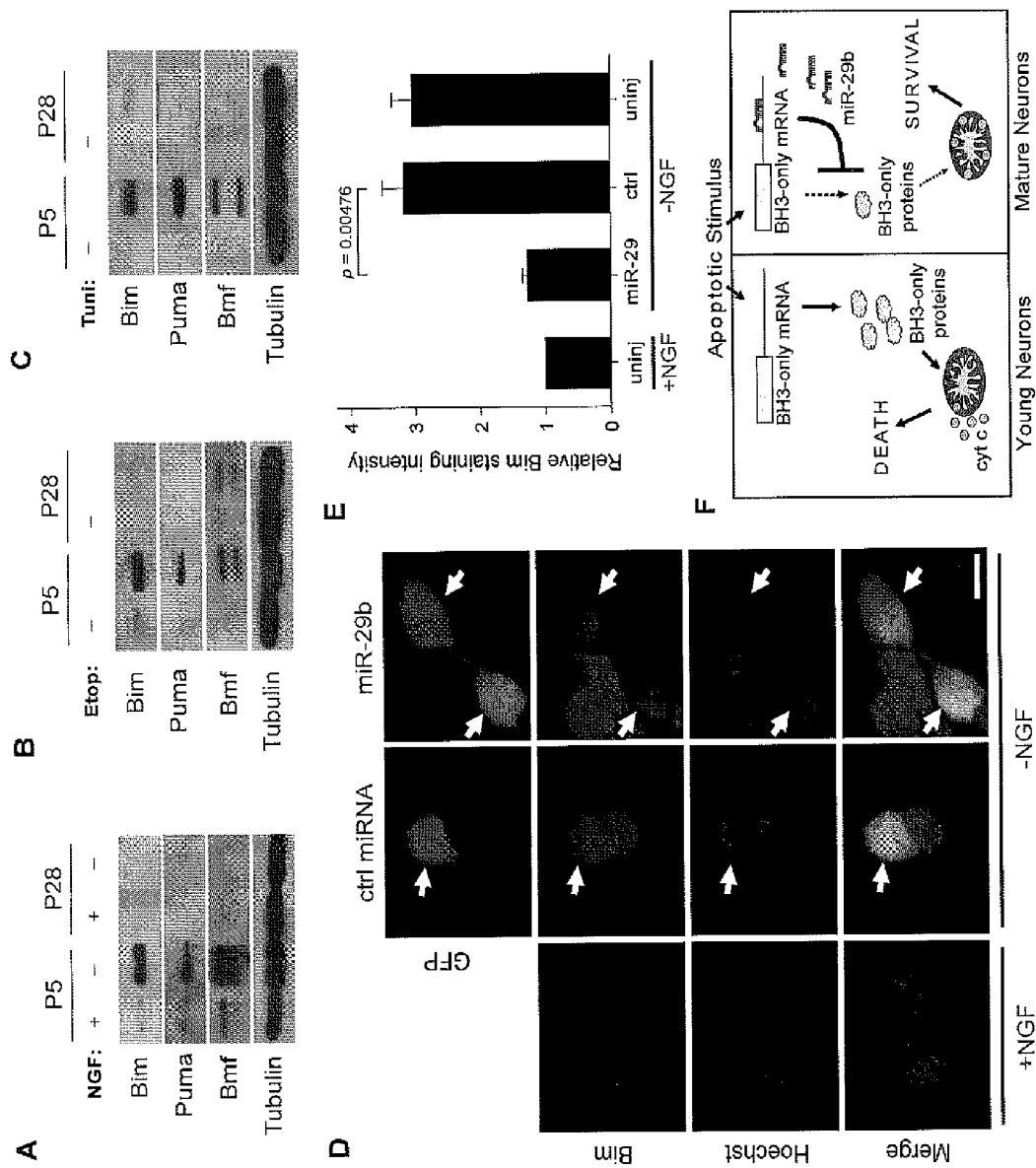
FIGS. 9A-9F show miR-29b expression in neurons blocks induction of endogenous BH3-only proteins. (A-C) The protein levels of $Bim_{EL}$, Bmf, and Puma were determined by Western blot in P0 neurons cultured for 5 days (P5) or 28 days (P28) in vitro. Neurons were either left untreated (+NGF) or deprived of NGF (−NGF) (A), untreated (−Etop) or treated with 20 μM etoposide (+Etop) (B), or untreated (−Tuni) or treated with 2.5 μM tunicamycin (+Tuni) (C). All treatments were performed for 48 hrs in the presence of the caspase inhibitor Q-VD-OPh (25 μM) before lysates were collected. Representative Western blots are shown. BMF isoforms were detected at ~25 kDa and ~30 kDa. (D, E) P3 sympathetic neurons were microinjected with a GFP-expressing plasmid and either miR-29b or cel-miR-67 (ctrl miRNA, each 30 μM). After 48 hrs, cells were left untreated (+NGF) or deprived of NGF (−NGF). Cells were fixed and stained 48 hrs after cell treatment. (D) Representative photographs of Bim staining in neurons; GFP expression indicates injected cells (arrows). Bar, 10 μm. (E) Fluorescence intensity of cells after Bim staining. Data are mean±s.e.m. of three independent experiments. F) Proposed model showing that high miR-29b levels in mature neurons prevent induction of BH3-only proteins after apoptotic stimuli. Apoptotic stimuli cause cytochrome c release and death in young neurons while mature neurons remain resistant.
Figure 10:
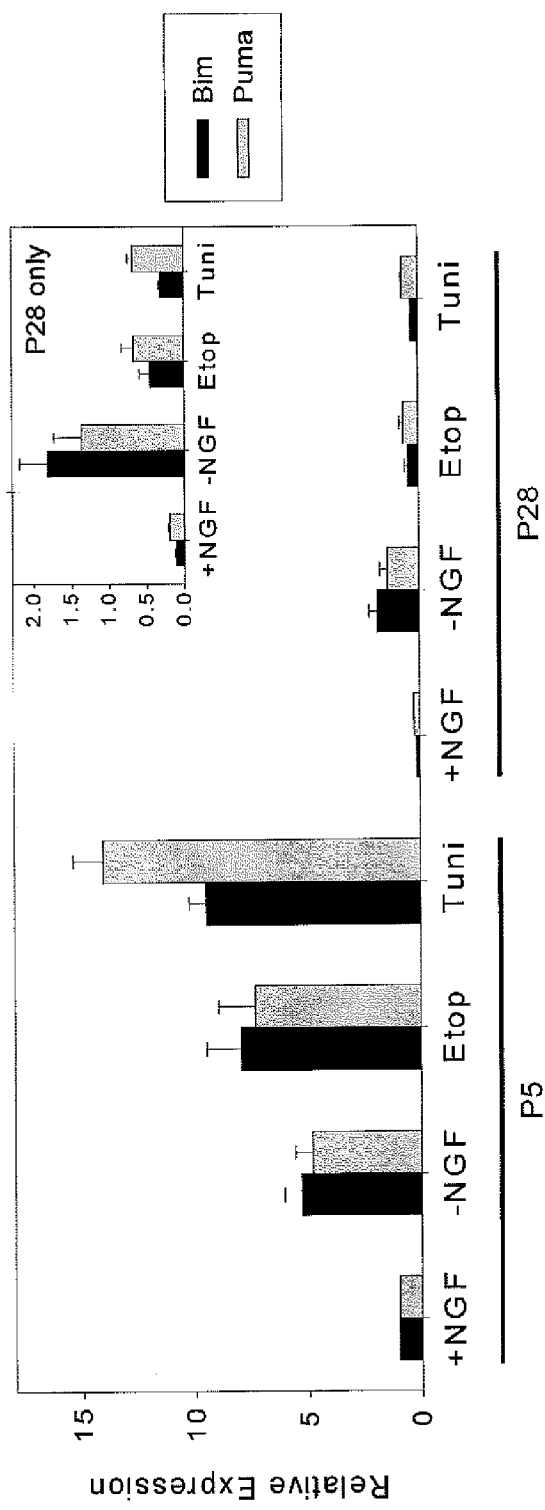
FIG. 10 shows induction of BH-3 only mRNAs upon apoptotic stimulation. qRT-PCR for Bim and Puma from P0 sympathetic neurons maintained in culture for 5 days (P5) or 28 days (P28). Neurons were either maintained in NGF (+NGF), or treated for 48 hrs with NGF deprivation (−NGF), 20 μM etoposide (Etop), or 2.5 μM tunicamycin (Tuni). Expression of each gene is plotted relative to levels in untreated P5 neurons. Inset shows relative expression of genes in P28 neurons only. Data are mean±s.e.m. of three independent experiments.

The observation that miR-29b is able to target the 3'UTRs of the BH3-only family of genes suggested to us that apoptosis is blocked in mature neurons due to the repression of BH3-only protein induction. Thus, we examined the status of several BH3-only proteins in P5 and mature P28 neurons after NGF deprivation or etoposide and tunicamycin treatment. Indeed, while Bim and Puma are induced after NGF deprivation in P5 neurons (Putcha et al., *Neuron* 29:615 (2001)), these proteins fail to be induced in P28 neurons (FIG. 9A). Equally important, while etoposide and tunicamycin treatment each robustly induced Bim and Puma in P5 neurons, an induction of these proteins was not seen in P28 neurons (FIGS. 9B and 9C). In addition, we found that Bmf, a BH3-only protein whose function has not yet been characterized in neurons, is also induced after all three treatments in P5 neurons, but not significantly in P28 neurons (FIGS. 9A-9C). miRNAs are known to suppress gene expression through a combination of mRNA cleavage and translational repression (Bartel, *Cell* 136:215 (2009)). Interestingly, although BH3-only mRNAs became induced in P28 neurons after each treatment, the amount of BH3-only mRNA that was detected in treated P28 neurons was as low as that seen in healthy P5 neurons (FIG. 10). Taken together, our data show that, in mature neurons, which have high endogenous levels of miR-29, the induction of BH3-only proteins is effectively blocked after multiple apoptotic insults.

A prediction of our model (FIG. 9F) is that expression of miR-29b should directly block the expression of BH3-only proteins in a situation where endogenous BH3-only proteins are induced. We tested this hypothesis in young P5 neurons and focused on Bim, since this is the best characterized BH3-only protein shown to be induced after NGF deprivation. As expected, injection of the control miRNA had no effect on the induction of Bim following NGF deprivation in P5 neurons. Strikingly, however, P5 neurons expressing miR-29b showed a marked reduction in Bim induction after NGF deprivation (FIGS. 9D and 9E). Together, these results show that miR-29b can block apoptosis in neurons by directly inhibiting at the critical step of BH3-only protein induction.

While it is important for developing neurons to be sensitive to apoptotic stimuli for proper formation of the nervous system, the apoptotic pathway must be strictly inhibited after development to ensure that mature neurons can survive long-term. The observation that Bax remains inactive in the cytoplasm after NGF deprivation in mature neurons has been described, though the molecules responsible for this phenomenon were unknown (Putcha et al., *J. Cell Biol.* 149:1011 (2000)). Here, we have identified miR-29b as a key molecule that is induced during neuronal maturation and functions to repress translation of the BH3-only family of proteins, thus preventing death in response to apoptotic stimuli. These results are the first to identify a mammalian miRNA which strictly inhibits apoptosis in normal, healthy neurons.

A recent study found that expression of the miR-29 family is reduced in sporadic Alzheimer's disease (AD) patients' brains (Hebert et al., *Proc. Natl. Acad. Sci, USA* 105:6415 (2008)). This study identified β site APP-cleaving enzyme 1 (BACE1), a critical molecule in the release of β-amyloid peptides from APP, as a target of MiR-29. Thus, loss of miR-29 expression in sporadic AD could lead to an increase in BACE1 expression and, ultimately, β-amyloid plaques, which are the characteristic protein aggregates of AD. Our results identifying miR-29b as an important inhibitor of apoptosis in neurons provide additional insight as to why loss of miR-29 expression may leave neurons more vulnerable to neurodegeneration, and emphasize the importance of miR-29 for long-term neuronal survival.

After cytotoxic stress, pro-apoptotic BH3-only proteins are crucial for triggering apoptosis by either inhibiting the anti-apoptotic proteins Bcl-2, Mcl-1, and Bcl-xL, or by directly activating pro-apoptotic Bax and Bak (Willis et al., *Curr. Opin. Cell Biol.* 17:617 (2005); Chipuk et al., *Trends Cell Biol.* 18:157 (2008)). In *C. elegans* only a single BH3-only protein, EGL-1 is necessary for activating apoptosis during development (Conradt et al., *Cell* 93:519 (1998)). In contrast, mammals contain at least eight BH3-only proteins, distinct subsets of which are activated after different apoptotic stimuli (Giam et al., *Oncogene* 27 *Suppl* 1:S128 (2008)). While this large repertoire of BH3-only proteins allows for increased regulation of apoptosis, it also leads to a redundancy in their function. In fact, loss of either Bim or Hrk alone in sympathetic neurons provides only a modest survival advantage over wild-type neurons (Putcha et al., *Neuron* 29:615 (2001); Imaizumi et al., *J. Neurosci.* 24:3721 (2004)). Thus, in order to efficiently inhibit apoptosis at the level of BH3-only activity, it is necessary to block multiple members of this pathway simultaneously. Indeed, we found that miR-29b is able to target at least five unique members of the BH3-only family. Interestingly, while we were unable to find predicted miR-29 binding sites in the 3'UTRs of Bid, Bad, or Noxa, evidence also shows that these BH3-only family members do not play a major role in sympathetic neurons (Putcha et al., *J. Cell Biol.* 157:441 (2002); Wyttenbach et al., *J. Neurochem.* 96:1213 (2006)).

Why would miR-29b evolve to inhibit apoptosis in neurons by repressing several BH3-only genes when, for example, targeting Bax alone would lead to similar, if not greater, resistance to apoptosis by intrinsic stimuli (Deckwerth et al., *Neuron* 17:401 (1996))? One possibility is that targeting Bax may have undesirable consequences because of its nonapoptotic role in regulating mitochondrial fusion (Karbowski et al. *Nature* 443:658 (2006))). Also, by targeting the BH3-only members of the Bcl-2 family, miR-29b may have evolved to fine-tune apoptosis regulation as opposed to completely disengaging apoptotic signaling.

Figure 11:
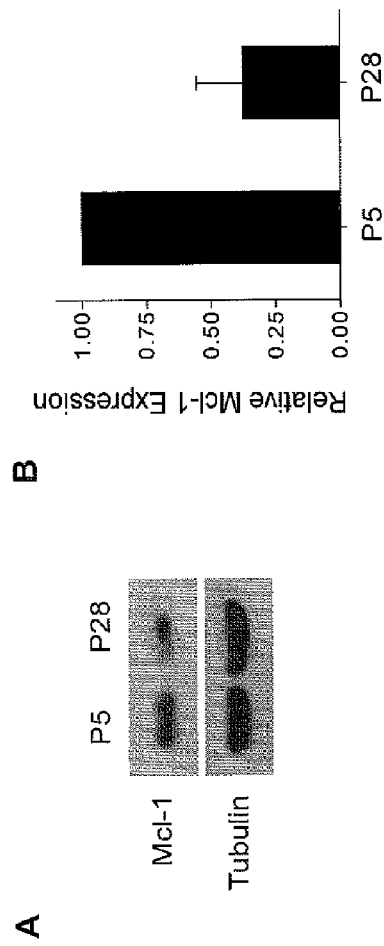
FIGS. 11A-11B show Mcl-1 levels are reduced during neuronal maturation. A) Protein levels of Mcl-1 were determined by Western blot in P0 neurons culture for 5 days (P5) or 28 days (P28) in vitro. B) Densitometric analysis of Mcl-1 levels in P5 and P28 neurons. Expression was calculated by normalizing Mcl-1 levels to tubulin, which served as a loading control. Mcl-1 expression is plotted relative to levels in P5 neurons. Data in (B) are mean±s.e.m. of three independent experiments.

Intriguingly, miR-29 function in cancer cells appears to be complex. While miR-29 expression is elevated in some cancers where it appears to function as an oncogene (Han et al., *J. Exp. Med.* 207:475 (2010); Gebeshuber et al., *EMBO Rep.* 10:400 (2009)), others have found miR-29 to have tumor suppressor functions (Pekarsky et al., *Cancer Res* 66:11590 (2006); Wang et al., *Cancer Cell* 14:369 (2008)), notably by targeting the anti-apoptotic protein Mcl-1 (Mott et al., *Oncogene* 26:6133 (2007)). We examined levels of Mcl-1 in P5 versus P28 neurons and found that in fact, Mcl-1 levels were paradoxically downregulated upon neuronal maturation, despite these neurons being strikingly resistant to apoptosis (FIG. 11). Thus, although the consequence of miR-29 expression in various cancer cells may depend on cellular context, its ability to inhibit the BH3-only family proteins has a clear anti-apoptotic function in primary neurons.

miRNAs have been described to modulate a variety of cellular processes including differentiation, proliferation, and apoptosis (Esquela-Kerscher et al., *Nat. Rev. Cancer* 6:259 (2006); Stefani et al., *Nat. Rev. Mol. Cell. Biol.* 9:219 (2008)), and they may regulate nearly two-thirds of the entire mammalian genome (Friedman et al., *Genome Res.* 19:92 (2009)). Our results here identify miR-29b to be induced during the physiologically normal process of neuronal maturation and demonstrate the ability of a single miRNA to inhibit apoptosis by targeting multiple members of a key pro-apoptotic gene family.

EXAMPLE 4

Screening Method for Modulators of miR-29b

Figure 12:
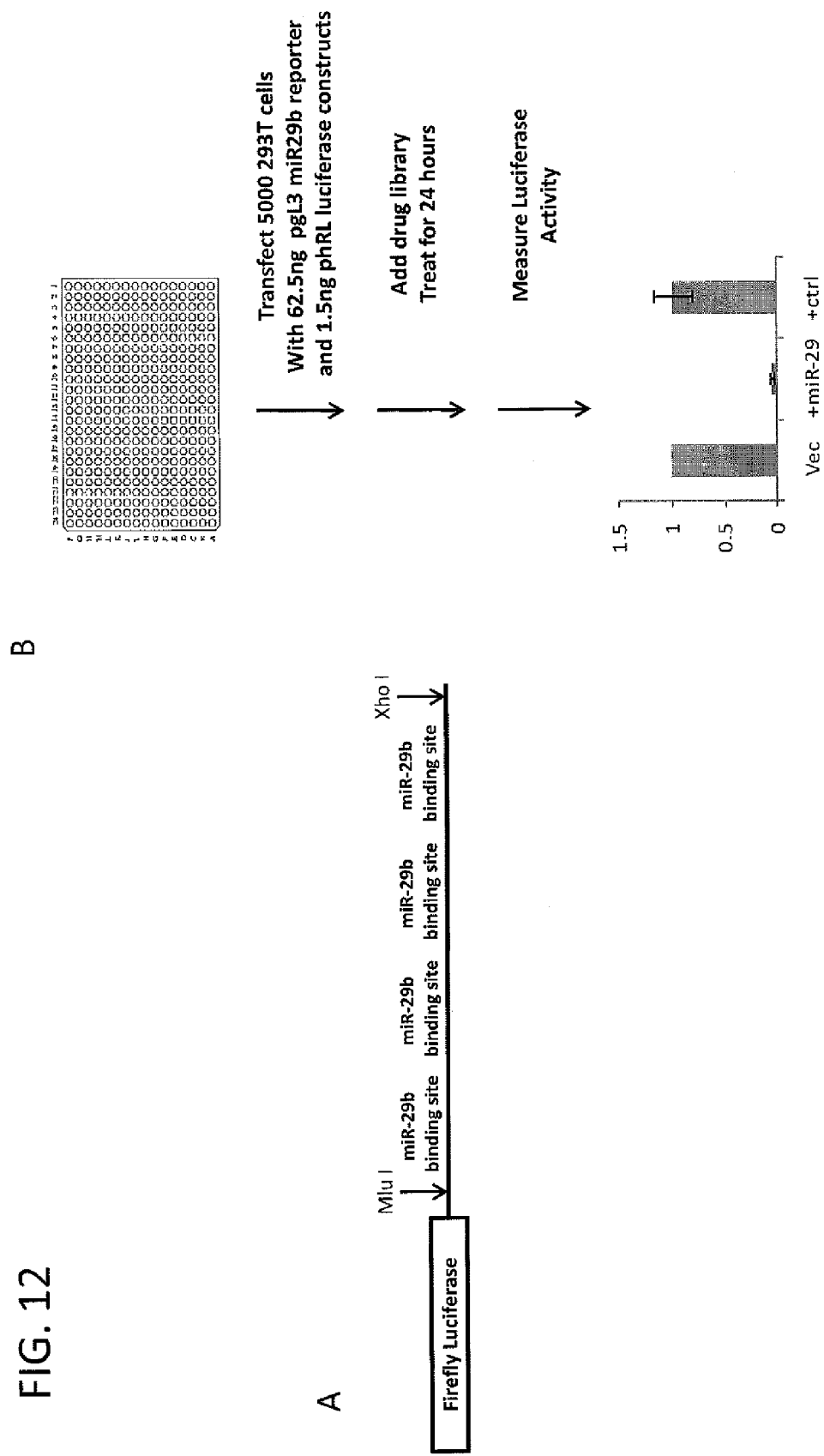
FIGS. 12A-12B show a screening method for modulation of miR-29b.

In order to develop a high throughput screening assay for modulators of miR-29b, a miR-29b reporter plasmid was constructed by cloning four perfect miR-29b binding sites into a modified pGL3-CM plasmid in which the multiple cloning site was placed downstream of the Firefly luciferase gene (the pGL3-CM plasmid was a kind gift from Dr. Da-Zhi Wang, UNC Chapel Hill) (FIG. 12A).

For the assay, 5000 293T cells are seeded into a 384-well plate. The pGL3-CM miR29b reporter plasmid expressing Firefly luciferase and a phRL control *Renilla* plasmid (Promega) are reverse transfected using the calcium phosphate precipitation method. Compounds that elevate miR-29 levels are anticipated to reduce Firefly luciferase signal. The *Renilla* luciferase plasmid serves as a control to identify compounds that simply reduce Firefly luciferase activity due to nonspecific toxicity. The library of small molecule compounds are added at the time of transfection and treatment continues for 24 hours. Firefly and *Renilla* Luciferase activity are then measured using the Dual-Glo Luciferase Assay Kit from Promega. Putative hits are defined as compounds which reduce Firefly Luciferase activity with no change to *Renilla* Luciferase (FIG. 12B).

Figure 13:
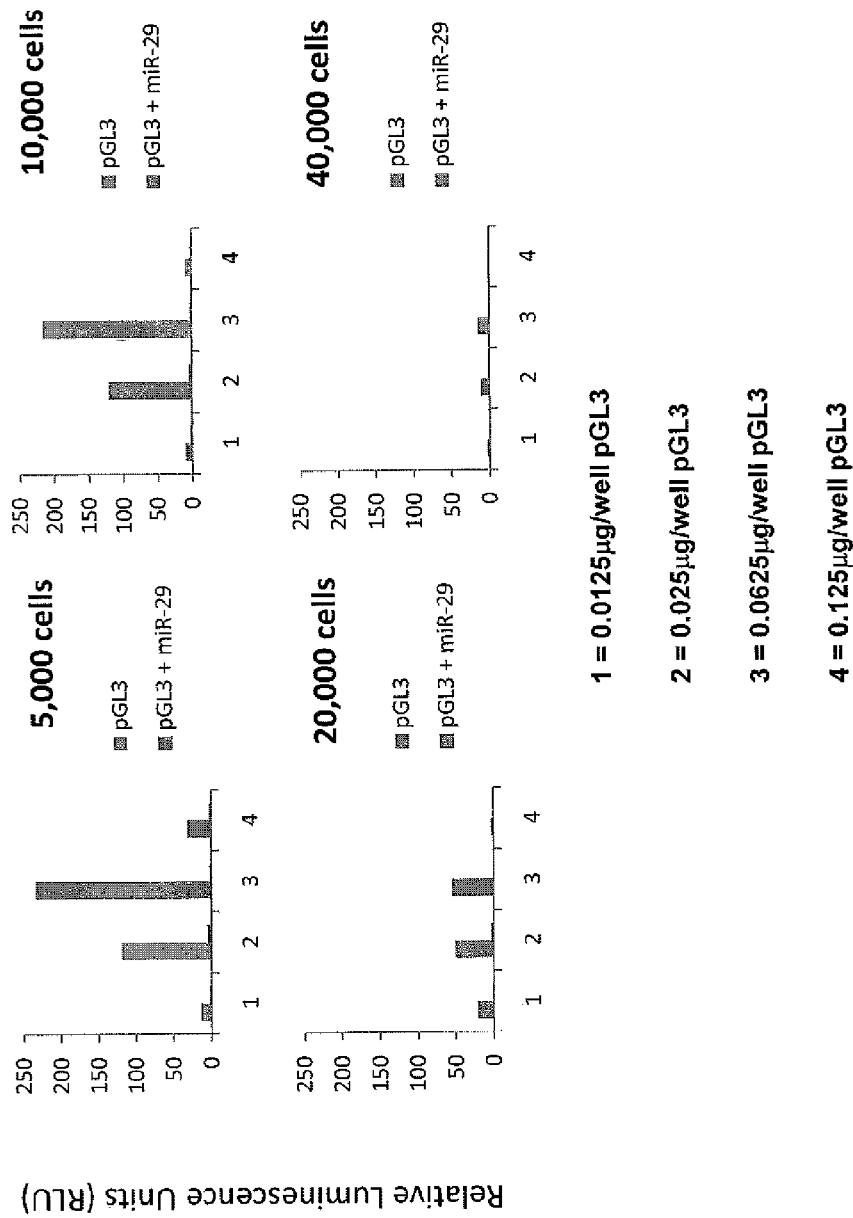
FIG. 13 shows data from a representative experiment.

Experiments have been conducted to optimize this assay to determine the optimal cell number, transfection conditions, and DMSO tolerance. For these experiments, miR-29 was used as a positive control to simulate a compound that would elevate miR-29 and reduce Firefly luciferase signal (from the pGL3-CM miR-29 reporter plasmid). Data from a representative experiment are shown in FIG. 13.

The foregoing is illustrative of the present invention, and is not to be construed as limiting thereof. The invention is defined by the following claims, with equivalents of the claims to be included therein.

---

That which is claimed is:

1. A method of inhibiting expression of one or more BH3-only genes in a cell, comprising increasing the amount of miR-29b in the cell.

2. The method of claim 1, wherein the cell is a post-mitotic cell.

3. The method of claim 1, wherein the cell is a neuron.

4. The method of claim 3, wherein the neuron is a central nervous system neuron.

5. The method of claim 4, wherein the neuron is a cerebellar neuron, cortical neuron, or motor neuron.

6. The method of claim 3, wherein the neuron is a peripheral nervous system neuron.

7. The method of claim 6, wherein the neuron is a sympathetic neuron or a dorsal root ganglia neuron.

8. The method of claim 1, wherein the BH3-only gene is selected from the group consisting of bim, hrk, bmf, puma, and N-bak.

9. The method of claim 1, wherein the expression of at least 3 BH3-only genes is inhibited.

10. A method of increasing the resistance of a cell to an apoptotic signal, comprising increasing the amount of miR-29b in the cell, wherein increasing the amount of miR-29b inhibits expression of one or more BH3-only genes in a cell.

11. The method of claim 10, wherein the apoptotic signal is deprivation of nerve growth factor, DNA damage, or endoplasmic reticulum damage.

12. A method of treating a disorder related to apoptosis in a subject, comprising increasing the amount of miR-29b in a cell of the subject, wherein increasing the amount of miR-29b inhibits expression of one or more BH3-only genes in the subject.

13. The method of claim 12, wherein the disorder related to apoptosis is a neurodegenerative disorder.

14. The method of claim 1, wherein increasing the amount of miR-29b in the cell comprises delivering miR-29b to the cell or delivering a vector encoding miR-29b to the cell.

15. The method of claim 1, wherein the miR-29b is encoded by an isolated polynucleotide.

16. The method of claim 15, wherein the isolated polynucleotide is integrated into a vector.

17. The method of claim 1, wherein the expression of at least 5 BH3-only genes is inhibited.

* * * * *

UNITED STATES PATENT AND TRADEMARK OFFICE
CERTIFICATE OF CORRECTION

PATENT NO.        : 8,618,073 B2                                          Page 1 of 1
APPLICATION NO.   : 13/811003
DATED             : December 31, 2013
INVENTOR(S)       : Deshmukh et al.

It is certified that error appears in the above-identified patent and that said Letters Patent is hereby corrected as shown below:

In the Specification:

Column 6, Line 22: Please correct "see also MPEP §2111.01 Thus"
 to read -- see also MPEP §2111.03. Thus --

Column 32, Line 65: Please correct "blots were performed"
 to read -- Western blots were performed --

Signed and Sealed this
Twenty-third Day of September, 2014

Michelle K. Lee
*Deputy Director of the United States Patent and Trademark Office*